United States Patent
Im et al.

(10) Patent No.: US 11,660,312 B2
(45) Date of Patent: May 30, 2023

(54) BIFIDOBACTERIUM BIFIDUM STRAIN AND STRAIN-DERIVED POLYSACCHARIDE

(71) Applicants: INSTITUTE FOR BASIC SCIENCE, Daejeon (KR); POSTECH ACADEMY-INDUSTRY FOUNDATION, Pohang-si (KR)

(72) Inventors: Sin-Hyeog Im, Pohang-si (KR); Ravi Verma, Pohang-si (KR); Changhon Lee, Pohang-si (KR)

(73) Assignees: INSTITUTE FOR BASIC SCIENCE, Daejeon (KR); POSTECH ACADEMY-INDUSTRY FOUNDATION, Pohang-si (KR)

( * ) Notice: Subject to any disclaimer, the term of this patent is extended or adjusted under 35 U.S.C. 154(b) by 601 days.

(21) Appl. No.: 16/621,442

(22) PCT Filed: Jun. 14, 2018

(86) PCT No.: PCT/KR2018/006700
§ 371 (c)(1),
(2) Date: Dec. 11, 2019

(87) PCT Pub. No.: WO2018/230960
PCT Pub. Date: Dec. 20, 2018

(65) Prior Publication Data
US 2021/0077521 A1   Mar. 18, 2021

(30) Foreign Application Priority Data
Jun. 14, 2017   (KR) .......................... 10-2017-0075079

(51) Int. Cl.
*A61K 31/716* (2006.01)
*A61K 35/745* (2015.01)
(Continued)

(52) U.S. Cl.
CPC .......... *A61K 31/716* (2013.01); *A61K 35/745* (2013.01); *A61P 29/00* (2018.01);
(Continued)

(58) Field of Classification Search
CPC .......... A61P 37/02; A61P 37/08; A61P 29/00; A61K 35/745
See application file for complete search history.

(56) References Cited

U.S. PATENT DOCUMENTS

| | | | |
|---|---|---|---|
| 2004/0147010 A1* | 7/2004 | Vidal | A61P 11/00 435/252.9 |
| 2015/0152454 A1 | 6/2015 | Miura | |
| 2017/0081428 A1 | 3/2017 | Siedlecki et al. | |

FOREIGN PATENT DOCUMENTS

| | | |
|---|---|---|
| EP | 1965809 | 9/2009 |
| JP | 2009-091255 | 4/2009 |

(Continued)

OTHER PUBLICATIONS

Yamazaki et al., "Dendritic cells as controllers of antigen-specific Foxp3+ regulatory T cells" Journal of Dermatological Sciences vol. 54 pp. 69-75 doi: 10.1016/j.jdermsci.2009.02.001 (Year: 2009).*

(Continued)

*Primary Examiner* — Eric Olson
(74) *Attorney, Agent, or Firm* — Lex IP Meister, PLLC

(57) ABSTRACT

The present invention relates to a *Bifidobacterium bifidum* inducing regulatory T cells (Treg), a polysaccharide derived from *Bifidobacterium bifidum*, and a probiotic strain producing a polysaccharide and, more particularly, a polysaccharide containing β-1-6-glucan as an effective ingredient, a probiotic strain producing β-1-6-glucan, a food comprising the polysaccharide or strain as an effective ingredient for alleviation of immune disease or inflammatory disease, a therapeutic agent comprising the polysaccharide or strain as an effective ingredient for alleviation of immune disease or (Continued)

inflammatory disease, a method for preparing induced regulatory T cells (iTreg) by treatment with the polysaccharide or strain, and a cell therapy product for prevention or treatment of immune disease or inflammatory disease, comprising the induced regulatory T cells prepared by the method.

9 Claims, 19 Drawing Sheets

Specification includes a Sequence Listing.

(51) Int. Cl.
| | |
|---|---|
| *C12N 1/20* | (2006.01) |
| *A61P 37/02* | (2006.01) |
| *A61P 37/08* | (2006.01) |
| *A61P 29/00* | (2006.01) |
| *C08B 37/00* | (2006.01) |
| *C08L 5/00* | (2006.01) |

(52) U.S. Cl.
CPC ............... *A61P 37/02* (2018.01); *A61P 37/08* (2018.01); *C08B 37/0024* (2013.01); *C08L 5/00* (2013.01); *C12N 1/205* (2021.05); *A23V 2200/324* (2013.01); *A23Y 2300/25* (2013.01); *Y10S 424/831* (2013.01)

(56) References Cited

FOREIGN PATENT DOCUMENTS

| | | |
|---|---|---|
| JP | 2013-521335 | 6/2013 |
| JP | 2016-128502 | 7/2016 |
| KR | 10-0720706 | 5/2007 |
| WO | 2009/134891 | 11/2009 |
| WO | 2014/136982 | 9/2014 |
| WO | 2015/172040 | 11/2015 |
| WO | 2016/118654 | 7/2016 |
| WO | 2016/209806 | 12/2016 |

OTHER PUBLICATIONS

Volman et al., "Dietary modulation of immune function by β-glucans" Physiology and Behavior vol. 94 pp. 276-284 doi: 10.1016/j.physbeh.2007.11.045 (Year: 2762).*
Rout et al., "The structure and conformation of a water-insoluble (1,3)-,(1,6)-b-D-glucan from the fruiting bodies of Pleurotus florida" Carbohydrate Research vol. 343 pp. 982-987 doi:10.1016/j.carres.2007.12.022 (Year: 2008).*
Palacios et al., "Novel isolation of water-soluble polysaccharides from the fruiting bodies of Pleurotus ostreatus mushrooms" Carbohydrate Research vol. 358 pp. 72-77 http://dx.doi.org/10.1016/j.carres.2012.06.016 (Year: 2012).*
Maniarora et al., "Analysis of Modulation of Foxp3 Expression in CD4 CD25 Regulatory Cells from NOD Mice" J. Ky. Acad. Sci. vol. 70 n0. 2 pp. 145-151 (Year: 2009).*
Speciale et al., "Bifidobacterium bifidum presents on the cell surface a complex mixture of glucans and galactans with different immunological properties" Carbohydrate Polymers vol. 218 pp. 269-278 (Year: 2019).*
Irene González-Rodríguez et al., "Role of Extracellular Transaldolase from Bifidobacterium bifidum in Mucin Adhesion and Aggregation", Applied and Environmental Microbiology, vol. 78, No. 11, p. 3992-3998.
KIPO, Final Office Action of KR 10-2018-0067535 dated May 28, 2020.
KIPO, Notice of Allowance of KR 10-2019-0086354 dated Feb. 28, 2020.
Koji Atarashi et al., "Induction of Colonic Regulatory T Cells by Indigenous Clostridium Species",Science. Jan. 21, 2011; 331(6015): 337-341. doi:10.1126/science.1198469.
Koji Atarashi et al. "Treg induction by a rationally selected mixture of Clostridia strains from the human microbiota", ., Nature, 2013, vol. 500, p. 232-236. doi:10.1038/nature12331.
B-H Yang et al., "Foxp3(+) T cells expressing RORγt represent a stable regulatory T-cell effector lineage with enhanced suppressive capacity during intestinal inflammation.", Mucosal immunology 9:444-457, 2016. doi:10.1038/mi.2015.74.
C. Preston Neff et al., "Diverse intestinal bacteria contain putative zwitterionic capsular polysaccharides with anti-inflammatory properties", Cell Host Microbe. Oct. 12, 2016; 20(4): 535-547. doi:10.1016/j.chom.2016.09.002.
Chang-Suk Chae et al., "Prophylactic Effect of Probiotics on the Development of Experimental Autoimmune Myasthenia Gravis", PLoS ONE, Dec. 2012, 7(12): e52119. doi:10.1371/journal.pone.0052119.
Chiara Ferrario et al., "A genome-based identification approach for members of the genus *Bifidobacterium*", FEMS Microbiology Ecology, 91, 2015, fiv009. doi: 10.1093/femsec/fiv009.
M.Choolani et al., "FastFISH: technique for ultrarapid fluorescence in situ hybridization on uncultured amniocytes yielding results within 2 h of amniocentesis", Molecular Human Reproduction vol. 13, No. 6 pp. 355-359, 2007. doi: 10.1093/molehr/gam016.
Brian A. Cobb et al., "Zwitterionic capsular polysaccharides: the new MHCII-dependent antigens", Cellular Microbiology (2005) 7(10), 1398-1403. doi:10.1111/j.1462-5822.2005.00591.x.
Dennis L. Kasper et al., "Capsular Polysaccharides and Lipopolysaccharides from Two Bacteroides fragilis Reference Strains: Chemical and Immunochemical Characterization", Journal of bacteriology 153: 991-997, 1983.
Danielle M. Tartar et al., "FoxP3+RORγt+ T Helper Intermediates Display Suppressive Function against Autoimmune Diabetes", The Journal of Immunology 184: 3377-3385, 2010. doi: 10.4049/jimmunol.0903324.
Claudia Di Giacinto et al., "Probiotics Ameliorate Recurrent Th1-Mediated Murine Colitis by Inducing IL-10 and IL-10-Dependent TGF-β-Bearing Regulatory Cells", The Journal of Immunology 174: 3237-3246, 2005. doi: 10.4049/jimmunol.174.6.3237.
Achmad Dinoto et al., "Population Dynamics of Bifidobacterium Species in Human Feces during Raffinose Administration Monitored by Fluorescence In Situ Hybridization-Flow Cytometry", Applied and Environmental Microbiology, Dec. 2006, p. 7739-7747. doi:10.1128/AEM.01777-06.
Michel Dubois et al., "Colorimetric Method for Determination of Sugars and Related Substances", Analytical chemistry 28:350-356, 1956.
Esen Sefik et al., "Individual intestinal symbionts induce a distinct population of RORγ+ regulatory T cells", Science. Aug. 28, 2015; 349(6251): 993-997. doi:10.1126/science.aaa9420.
F. Powrie, "T Cells in Inflammatory Bowel Disease: Protective and Pathogenic Roles", Immunity 3:171-174, 1995.
Francesca Turroni et al., "Genome analysis of Bifidobacterium bifidum PRL2010 reveals metabolic pathways for host-derived glycan foraging", PNAS. 2010, vol. 107, No. 45, pp. 19514-19519.
Daisuke Fujiwara et al., "The Anti-Allergic Effects of Lactic Acid Bacteria Are Strain Dependent and Mediated by Effects on both Th1/Th2 Cytokine Expression and Balance", Int Arch Allergy Immunol 2004;135:205-215. DOI: 10.1159/000081305.
Yukihiro Furusawa et al., "Commensal microbe-derived butyrate induces the differentiation of colonic regulatory T cells", Nature, 2013. doi: 10.1038/nature12721.
Sassaki, Guilherme L. et al., "Pustulan and branched beta-gatactofuranan from the phytopathogenic fungus *Guignardia citricarpa*, excreted from media containing glucose and sucrose", Carbohydrate Polymers 48(2002) 385-389.
Gaboriau-Routhiau V et al., "The key role of segmented filamentous bacteria in the coordinated maturation of gut helper T cell responses", Immunity 31, 677-689, Oct. 16, 2009. DOI 10.1016/j.immuni.2009.08.020.
Shohei Hori et al., "Control of Regulatory T Cell Development by the Transcription Factor Foxp3", Science, vol. 299: 1057-1061, 2003. DOI: 10.1126/science.1079490.

(56) References Cited

OTHER PUBLICATIONS

Im, Sin-Hyeog, "Reprogramming of the Immune System by Rationally Selected Probiotics", abstract only, Institute for Basic Science (IBS) Jun. 7, 2018.
Ivaylo I. Ivanov et al., "Induction of intestinal Th17 cells by segmented filamentous bacteria", Cell. Oct. 30, 2009; 139(3): 485-498. doi:10.1016/j.cell.2009.09.033.
Ivaylo I. Ivanov et al., "Intestinal commensal microbes as immune modulators", Cell Host Microbe. Oct. 18, 2012; 12(4): 496-508. doi:10.1016/j.chom.2012.09.009.
Ana Izcue et al., "Regulatory Lymphocytes and Intestinal Inflammation", Annu. Rev. Immunol. 2009. 27:313-38. doi: 10.1146/annurev.immunol.021908.132657.
June L. Round et al., "The Toll-like receptor pathway establishes commensal gut colonization", Science. May 20, 2011; 332(6032): 974-977. doi: 10.1126/science.1206095.
Jonathan M. Weiss et al., "Neuropilin 1 is expressed on thymus-derived natural regulatory T cells, but not mucosagenerated induced Foxp3+ T reg cells", The Journal of Experimental Medicine, 2012 vol. 209 No. 10 1723-1742.
Justin P. Edwards et al., "Release of Active TGF-β1 from the Latent TGF-β1/GARP Complex on T Regulatory Cells Is Mediated by Integrin β8", J Immunol 2014; 193:2843-2849. doi: 10.4049/jimmunol.1401102.
Wiltrud M. Kalka-Moll et al., "Effect of Molecular Size on the Ability of Zwitterionic Polysaccharides to Stimulate Cellular Immunity", J Immunol Jan. 15, 2000, 164 (2) 719-724. doi: 10.4049/jimmunol.164.2.719.
Khalil Karimi et al., "Lactobacillus reuteri-induced Regulatory T cells Protect against an Allergic Airway Response in Mice", Am J Respir Crit Care Med vol. 179. pp. 186-193, 2009. DOI: 10.1164/rccm.200806-951OC.
Jung-Eun Kim et al., "Lactobacillus helveticus suppresses experimental rheumatoid arthritis by reducing inflammatory T cell responses", journal of functional foods 13( 2 0 1 5 ) 350-362.
Kwang Soon Kim et al., "Dietary antigens limit mucosal immunity by inducing regulatory T cells in the small intestine", Science. 2016. doi: 10.1126/science.aac5560.
Ho-Keun Kwon et al., "Generation of regulatory dendritic cells and CD4+Foxp3+ T cells by probiotics administration suppresses immune disorders", PNAS 107: 2159-2164, 2010. doi: 10.1073/pnas.0904055107.
Ho-Keun Kwon et al., "Amelioration of experimental autoimmune encephalomyelitis by probiotic mixture is mediated by a shift in T helper cell immune response", Clinical Immunology (2013) 146, 217-227.
Sarah Lebeer et al., "Anti-inflammatory potential of probiotics: lipoteichoic acid makes a difference", Trends in Microbiology Jan. 2012, vol. 20, No. 1. doi:10.1016/j.tim.2011.09.004.
Hong-Ying Liao et al., "Clostridium butyricum in combination with specific immunotherapy converts antigenspecific B cells to regulatory B cells in asthmatic patients", Scientific reports, 6: 20481, 2016. DOI: 10.1038/srep20481.
Matthias Lochner et al., "In vivo equilibrium of proinflammatory IL-17+ and regulatory IL-10+ Foxp3+ RORgamma t+T cells", J Exp Med. Jun. 9, 2008;205(6):1381-93. doi: 10.1084/jem.20080034.
Patricia Lopez et al., "Immune Response to Bifidobacterium bifidum Strains Support Treg/Th17 Plasticity", PLoS ONE 6(9): e24776. doi:10.1371/journal.pone.0024776.
A. Lyons et al., "Bacterial strain-specific induction of Foxp31 T regulatory cells is protective in murine allergy models", Clinical & Experimental Allergy, 40, 811-819. doi: 10.1111/j.1365-2222.2009.03437.x.
Marianna Esposito et al., "IL-17- and IFN-g-Secreting Foxp3+ T Cells Infiltrate the Target Tissue in Experimental Autoimmunity", J Immunol. Dec. 15, 2010;185(12):7467-73. doi: 10.4049/jimmunol.1001519.

Andrew J.Macpherson et al., "Interactions between commensal intestinal bacteria and the immune system", Nature Reviews Immunology 4: 478-485, 2004.
Sarkis K. Mazmanian et al., "An Immunomodulatory Molecule of Symbiotic Bacteria Directs Maturation of the Host Immune System", Cell, vol. 122, 107-118, Jul. 15, 2005. DOI 10.1016/j.cell.2005.05.007.
Nicholas Arpaia et al., "Metabolites produced by commensal bacteria promote peripheral regulatory T cell generation", Nature. Dec. 19, 2013; 504(7480): 451-455. doi: 10.1038/nature12726.
Ethan M Shevach et al., "tTregs, pTregs, and iTregs: Similarities and Differences", Immunol Rev. May 2014 ; 259(1): 88-102. doi:10.1111/imr.12160.
Javier Ochoa-Repáraz et al., "Central Nervous System Demyelinating Disease Protection by the Human Commensal Bacteroides fragilis Depends on Polysaccharide A Expression", J Immunol 2010; 185:4101-4108. doi: 10.4049/jimmunol.1001443.
June L. Round et al., "Inducible Foxp3+ regulatory T-cell development by a commensal bacterium of the intestinal microbiota", PNAS Jul. 6, 2010 107 (27) 12204-12209. doi: 10.1073/pnas.0909122107.
June L. Round et al., "The gut microbiome shapes intestinal immune responses during health and disease", Nat Rev Immunol. May 2009 ; 9(5): 313-323. doi: 10.1038/nri2515.
Tze Guan Tan et al., "Identifying species of symbiont bacteria from the human gut that, alone, can induce intestinal Th17 cells in mice", PNAS Dec. 13, 2016 113 (50) E8141-E8150. doi: 10.1073/pnas.1617460113.
Takeshi Tanoue et al., "Development and maintenance of intestinal regulatory T cells", Nat Rev Immunol. May 2016;16(5):295-309. doi: 10.1038/nri.2016.36.
Kiel M Telesford et al., "A commensal symbiotic factor derived from Bacteroides fragilis promotes human CD39+Foxp3+ T cells and Treg function", Gut Microbes, 6:4, 234-242, DOI: 10.1080/19490976.2015.1056973.
KIPO, Office Action of KR 10-2020-0081537 dated Sep. 12, 2020.
Subha Karumuthil-Melethil et al., "Fungal b-Glucan, a Dectin-1 Ligand, Promotes Protection from Type 1 Diabetes by Inducing Regulatory Innate Immune Response", The Journal of Immunology, vol. 205, Issue 10, Nov. 15, 2020.
Subha Karumuthil-Melethil et al., "Fungal beta-Glucan, a Dectin-1 Ligand, Promotes Protection from Type 1 Diabetes by Inducing Regulatory Innate Immune Response", J Immunol Aug. 20, 2014, 1400186; DOI: https://doi.org/10.4049/jimmunol.1400186.
JPO, Office Action of JP 2019-569943 dated Dec. 22, 2020.
KIPO, Notice of Allowance of KR 10-2018-0067535 dated Dec. 29, 2020.
Ilka Noss et al., "Comparison of the potency of a variety of beta-glucans to induce cytokine production in human whole blood", Innate Immunity vol. 19, No. 1, Feb. 1, 2013.
Ifat Rubin-Bejerano et al., "Phagocytosis by human neutrophils is stimulated by a unique fungal cell wall component", Cell Host & Microbe vol. 2 No. 1, pp. 55-67, Jul. 12, 2007.
Smiderle et al., "Polysaccharides from Agaricus bisporus and Agaricus brasiliensis show similarities in their structures and their immunomodulatory effects on human monocytic THP-1 cells", BMC Complementary & Alternative Medicine, vol. 11, No. 1, Jul. 25, 2011.
EPO, Supplementary Partial Search Report of application No. 18817528.5, dated Feb. 16, 2021.
Francesca Turroni et al., "Exploring the Diversity of the Bifidobacterial Population in the Human Intestinal Tract", Appl Environ Microbiol. Mar. 2009;75(6):1534-45. doi: 10.1128/AEM.02216-08.
Verena K. Raker et al, "Tolerogenic Dendritic Cells for Regulatory T Cell induction in Man", Front Immunol. Nov. 9, 2015;6:569. doi: 10.3389/fimmu.2015.00569.
Ravi Verma et al., "Real-time analysis of mucosal flora in patients with inflammatory bowel disease in India", J Clin Microbiol. Nov. 2010;48(11):4279-82. doi: 10.1128/JCM.01360-10.
Walter J. Lukiw, "Bacteroides fragilis Lipopolysaccharide and Inflammatory Signaling in Alzheimer's Disease", Front. Microbiol. 2016; 7:1544. doi: 10.3389/fmicb.2016.01544.

(56) References Cited

OTHER PUBLICATIONS

Wei Wang et al., "Increased Proportions of Bifidobacterium and the Lactobacillus Group and Loss of Butyrate-Producing Bacteria in Inflammatory Bowel Disease", J Clin Microbiol. Feb. 2014;52(2):398-406. doi: 10.1128/JCM.01500-13.
Werner Fischer et al., "'Lipoteichoic acid' of Bifidobacterium bifidum subspecies pennsylvanicum DSM 20239", Eur. J. Biochem. 165,639-646 (1987).
Hsin-Jung Wu et al., "Gut-residing segmented filamentous bacteria drive autoimmune arthritis via T helper 17 cells", Immunity. Jun. 25, 2010; 32(6): 815-827. doi:10.1016/j.immuni.2010.06.001.
Hsin-Jung Wu et al., "The role of gut microbiota in immune homeostasis and autoimmunity", Gut microbes 3: 4-14, 2012.
Yingzi Cong et al., "Colitis Induced by Enteric Bacterial Antigen-Specific CD4+ T Cells Requires CD40-CD40 Ligand Interactions for a Sustained Increase in Mucosal IL-12", J Immunol Aug. 15, 2000, 165 (4) 2173-2182. doi: 10.4049/jimmunol.165.4.2173.
Yue Shen et al., "Outer Membrane Vesicles of a Human Commensal Mediate Immune Regulation and Disease Protection", Cell Host Microbe. Oct. 18, 2012; 12(4): 509-520. doi:10.1016/j.chom.2012.08.004.
Yingzi Cong et al., "A dominant, coordinated T regulatory cell-IgA response to the intestinal microbiota", PNAS Nov. 17, 2009 106 (46) 19256-19261; https://doi.org/10.1073/pnas.0812681106.
Ryu Yoshida et al., "A new method for quantitative analysis of the mouse T-cell receptor V region repertoires: comparison of repertoires among strains", Immunogenetics (2000) 52: 35-45. https://doi.org/10.1007/s002510000248.
KIPO., Office Action of KR 10-2018-0067535 dated May 27, 2019.
KIPO., Office Action of KR 10-2018-0067535 dated Nov. 21, 2019.
KIPO., Office Action of KR 10-2019-0086354 dated Aug. 21, 2019.
JPO, Notice of Allowance of JP 2021-047489 dated Mar. 2, 2023.

\* cited by examiner

B

B continued

SEQUENCE LISTING

<160> NUMBER OF SEQ ID NOS: 27

<210> SEQ ID NO 1
<211> LENGTH: 19
<212> TYPE: DNA
<213> ORGANISM: Artificial Sequence

```
<220> FEATURE:
<223> OTHER INFORMATION: EUB-f

<400> SEQUENCE: 1
tcctacggga ggcagcagt                                              19

<210> SEQ ID NO 2
<211> LENGTH: 26
<212> TYPE: DNA
<213> ORGANISM: Artificial Sequence
<220> FEATURE:
<223> OTHER INFORMATION: EUB-r

<400> SEQUENCE: 2
ggactaccag ggtatctaat cctgtt                                      26

<210> SEQ ID NO 3
<211> LENGTH: 21
<212> TYPE: DNA
<213> ORGANISM: Artificial Sequence
<220> FEATURE:
<223> OTHER INFORMATION: BibiF- (forward)

<400> SEQUENCE: 3
ccacatgatc gcatgtgatt g                                           21

<210> SEQ ID NO 4
<211> LENGTH: 19
<212> TYPE: DNA
<213> ORGANISM: Artificial Sequence
<220> FEATURE:
<223> OTHER INFORMATION: BibiF- (reverse)

<400> SEQUENCE: 4
ccgaaggctt gctcccaaa                                              19

<210> SEQ ID NO 5
<211> LENGTH: 21
<212> TYPE: DNA
<213> ORGANISM: Artificial Sequence
<220> FEATURE:
<223> OTHER INFORMATION: Bbif

<400> SEQUENCE: 5
ccacaatcac atgcgatcat g                                           21

<210> SEQ ID NO 6
<211> LENGTH: 21
<212> TYPE: DNA
<213> ORGANISM: Artificial Sequence
<220> FEATURE:
<223> OTHER INFORMATION: HPRT (forward)

<400> SEQUENCE: 6
ttatggacag gactgaaaga c                                           21

<210> SEQ ID NO 7
<211> LENGTH: 22
<212> TYPE: DNA
<213> ORGANISM: Artificial Sequence
<220> FEATURE:
<223> OTHER INFORMATION: HPRT (reverse)

<400> SEQUENCE: 7
gctttaatgt aatccagcag gt                                          22
```

-continued

```
<210> SEQ ID NO 8
<211> LENGTH: 20
<212> TYPE: DNA
<213> ORGANISM: Artificial Sequence
<220> FEATURE:
<223> OTHER INFORMATION: IL-10 (forward)

<400> SEQUENCE: 8
ataactgcac ccacttccca                                               20

<210> SEQ ID NO 9
<211> LENGTH: 20
<212> TYPE: DNA
<213> ORGANISM: Artificial Sequence
<220> FEATURE:
<223> OTHER INFORMATION: IL-10 (reverse)

<400> SEQUENCE: 9
tcatttccga taaggcttgg                                               20

<210> SEQ ID NO 10
<211> LENGTH: 19
<212> TYPE: DNA
<213> ORGANISM: Artificial Sequence
<220> FEATURE:
<223> OTHER INFORMATION: TGF-b (forward)

<400> SEQUENCE: 10
ctcccgtggc ttctagtgc                                                19

<210> SEQ ID NO 11
<211> LENGTH: 22
<212> TYPE: DNA
<213> ORGANISM: Artificial Sequence
<220> FEATURE:
<223> OTHER INFORMATION: TGF-b (reverse)

<400> SEQUENCE: 11
gccttagttt ggacaggatc tg                                            22

<210> SEQ ID NO 12
<211> LENGTH: 22
<212> TYPE: DNA
<213> ORGANISM: Artificial Sequence
<220> FEATURE:
<223> OTHER INFORMATION: IL-b (forward)

<400> SEQUENCE: 12
caaccaacaa gtgatattct cc                                            22

<210> SEQ ID NO 13
<211> LENGTH: 20
<212> TYPE: DNA
<213> ORGANISM: Artificial Sequence
<220> FEATURE:
<223> OTHER INFORMATION: IL-b (reverse)

<400> SEQUENCE: 13
tgccgtcttt cattacacag                                               20

<210> SEQ ID NO 14
<211> LENGTH: 20
<212> TYPE: DNA
<213> ORGANISM: Artificial Sequence
<220> FEATURE:
<223> OTHER INFORMATION: Csf2 (forward)
```

<400> SEQUENCE: 14
agggtctacg gggcaatttc                                          20

<210> SEQ ID NO 15
<211> LENGTH: 23
<212> TYPE: DNA
<213> ORGANISM: Artificial Sequence
<220> FEATURE:
<223> OTHER INFORMATION: Csf2 (reverse)

<400> SEQUENCE: 15
ggcagtatgt ctggtagtag ctg                                      23

<210> SEQ ID NO 16
<211> LENGTH: 21
<212> TYPE: DNA
<213> ORGANISM: Artificial Sequence
<220> FEATURE:
<223> OTHER INFORMATION: PD-L1 (forward)

<400> SEQUENCE: 16
gctccaaagg acttgtacgt g                                        21

<210> SEQ ID NO 17
<211> LENGTH: 21
<212> TYPE: DNA
<213> ORGANISM: Artificial Sequence
<220> FEATURE:
<223> OTHER INFORMATION: PD-L1 (reverse)

<400> SEQUENCE: 17
tgatctgaag ggcagcattt c                                        21

<210> SEQ ID NO 18
<211> LENGTH: 21
<212> TYPE: DNA
<213> ORGANISM: Artificial Sequence
<220> FEATURE:
<223> OTHER INFORMATION: IDO (forward)

<400> SEQUENCE: 18
gctttgctct accacatcca c                                        21

<210> SEQ ID NO 19
<211> LENGTH: 19
<212> TYPE: DNA
<213> ORGANISM: Artificial Sequence
<220> FEATURE:
<223> OTHER INFORMATION: IDO (reverse)

<400> SEQUENCE: 19
caggcgctgt aacctgtgt                                           19

<210> SEQ ID NO 20
<211> LENGTH: 22
<212> TYPE: DNA
<213> ORGANISM: Artificial Sequence
<220> FEATURE:
<223> OTHER INFORMATION: COX2 (forward)

<400> SEQUENCE: 20
tggctgcaga attgaaagcc ct                                       22

<210> SEQ ID NO 21
<211> LENGTH: 22
<212> TYPE: DNA
<213> ORGANISM: Artificial Sequence
<220> FEATURE:
<223> OTHER INFORMATION: COX2 (reverse)

<400> SEQUENCE: 21
aaaggtgctc ggcttccagt at                                            22

<210> SEQ ID NO 22
<211> LENGTH: 21
<212> TYPE: DNA
<213> ORGANISM: Artificial Sequence
<220> FEATURE:
<223> OTHER INFORMATION: CD80 (forward)

<400> SEQUENCE: 22
acccccaaca taactgagtc t                                             21

<210> SEQ ID NO 23
<211> LENGTH: 21
<212> TYPE: DNA
<213> ORGANISM: Artificial Sequence
<220> FEATURE:
<223> OTHER INFORMATION: CD80 (reverse)

<400> SEQUENCE: 23
ttccaaccaa gagaagcgag g                                             21

<210> SEQ ID NO 24
<211> LENGTH: 20
<212> TYPE: DNA
<213> ORGANISM: Artificial Sequence
<220> FEATURE:
<223> OTHER INFORMATION: CD86 (forward)

<400> SEQUENCE: 24
tgtttccgtg gagacgcaag                                               20

<210> SEQ ID NO 25
<211> LENGTH: 23
<212> TYPE: DNA
<213> ORGANISM: Artificial Sequence
<220> FEATURE:
<223> OTHER INFORMATION: CD86 (reverse)

<400> SEQUENCE: 25
cagctcactc aggcttatgt ttt                                           23

<210> SEQ ID NO 26
<211> LENGTH: 18
<212> TYPE: DNA
<213> ORGANISM: Artificial Sequence
<220> FEATURE:
<223> OTHER INFORMATION: CD40 (forward)

<400> SEQUENCE: 26
ccttgcactg tgaggaga                                                 18

<210> SEQ ID NO 27
<211> LENGTH: 20
<212> TYPE: DNA
<213> ORGANISM: Artificial Sequence
<220> FEATURE:
<223> OTHER INFORMATION: CD40 (reverse)

```
<400> SEQUENCE: 27
cttcgcttac aacgtgtgct                                           20
```

BIFIDOBACTERIUM BIFIDUM STRAIN AND STRAIN-DERIVED POLYSACCHARIDE

TECHNICAL FIELD

The present invention relates to *Bifidobacterium bifidum* inducing regulatory T (Treg) cells, a polysaccharide derived from *Bifidobacterium bifidum*, and a probiotic strain producing the polysaccharide, and more particularly to a polysaccharide including β-1-6-glucan as an active ingredient, a probiotic strain producing β-1-6-glucan, a food or therapeutic agent for the alleviation of an immune disease or an inflammatory disease comprising the polysaccharide or the strain as an active ingredient, a method of producing induced regulatory T (iTreg) cells by treatment with the polysaccharide or the strain, and a cellular therapeutic agent for preventing or treating an immune disease or an inflammatory disease comprising induced regulatory T cells produced thereby.

BACKGROUND ART

In the gastrointestinal tract of mammals, numerous species of bacteria constituting "microbiota" live in symbiosis. Changes in microbiota are closely related to various diseases such as allergic diseases and autoimmune and gastrointestinal inflammatory disorders. Compared to specific pathogen free (SPF) mice, germ free (GF) mice show abnormal responses to formation of lymphatic tissue and immune responses (Macpherson and Harris, *Nature Reviews Immunology* 4: 478-485, 2004), and these phenomena can be overcome by the introduction of commensal microorganisms (Mazmanian et al., *Cell* 122: 107-118, 2005). Intestinal microorganisms regulate the development and differentiation of specific lineages of CD4 T cells such as T helper 17 (Th17) cells or regulatory T (Treg) cells (Ivanov and Honda, *Cell host & microbe* 12: 496-508, 2012; Wu and Wu, *Gut microbes* 3: 4-14, 2012) (Atarashi et al., *Science* 331: 337-341, 2011; Macpherson and Harris, *Nature Reviews Immunology* 4: 478-485, 2004; Round and Mazmanian, *Nature Reviews Immunology* 9: 313-323, 2009). Treg cells are a subset of $CD4^+$ T cells with inhibitory functions, and are characterized by the expression of the transcription factor Foxp3 (S. Hori et al., *Science* 299: 1057-1061, 2003). Treg cells are generally formed in the thymus (nTreg) but can also occur in the vicinity of normal $CD4^+$ cells (pTreg).

Recently, individual species of the microbial community have been shown to form immune components of the host. In other words, Tregs and Th17 cells interact to regulate the host's immune response to various antigens. For example, segmented filamentous bacteria (SFB) strongly induce Th17 cells in the small intestine, which promote systemic autoimmunity and play an important role in host resistance to intestinal pathogens (Gaboriau-Routhiau et al., *Immunity* 31: 677-689, 2009; Ivanov et al., *Cell* 139: 485-498, 2009; Wu et al., *Immunity* 32: 815-827, 2010). In contrast, some of the strains constituting the intestinal flora and some probiotic strains are known to affect the differentiation, accumulation and function of Treg cells in the mouse colon (Tanoue, T et al., *Nature reviews Immunology* 16: 295-309, 2016). $CD4^+$ regulatory T cells (Tregs) expressing the transcription factor Foxp3 (forkhead box P3) are found more in the digestive lamina propria (LP), especially in the large intestine, compared to other organs (Atarashi et al., *Science* 331:337-341, 2011). Several studies have shown that the number and function of mucosal $Foxp3^+$ Tregs is affected by the presence of certain intestinal bacteria. A mixture of 17 strains belonging to the IV, XIVa, and XVIII clusters of Clostridia improved the differentiation, accumulation and function of Treg cells in the mouse large intestine (Atarashi et al., *Nature* 500: 232-236, 2013). Mice treated daily with probiotic bacteria, namely Bifidobacteria and Lactobacilli, exhibit an altered inflammatory state through the induction of Tregs (Di Giacinto et al., *The Journal of Immunology* 174: 3237-3246, 2005; Karimi et al., *American journal of respiratory and critical care medicine* 179: 186-193, 2009; Lyons et al., *Clinical & Experimental Allergy* 40: 811-819, 2010). Colonization of mice with the human symbiotic *Bacteroides fragilis* strengthens Th1 and IL-10 that produce Treg cells (Round and Mazmanian, PNAS 107: 12204-12209, 2010; Telesford et al., *Gut microbes* 6: 234-242, 2015). Previous studies have shown that IRT5, a mixture of five probiotic bacteria, can induce Treg cells and inhibit various immune diseases (Chae et al., *PloS One* 7, e52119, 2012; Kwon et al., Clinical Immunology 146: 217-227, 2013; Kwon et al., *PNAS* 107: 2159-2164, 2010). However, the basic molecular mechanism of Treg cell production is not yet clear. Various studies have shown that metabolites or cell wall components produced by bacteria can promote the differentiation of Treg cells. For example, butyrate has been reported as a major effector molecule inducing colonic Treg cells by Clostridia (Furusawa et al., *Nature* 504: 446-450, 2013). Polysaccharide A (PSA), which is a zwitterionic polysaccharide of *B. fragilis*, has been identified as a vital immunomodulatory agent for inducing Treg-producing IL-10 (Mazmanian et al., *Cell* 122:107-118, 2005; Ochoa-Reparaz et al., *The Journal of Immunology* 185:4101-4108, 2010). Administration of insufficient major microorganisms to patients, may be restore dysbiosis of dysregulated microorganisms. For example, transferring fecal microbiota (FMT) from healthy donors to patients has been reported to have a beneficial effect on gastrointestinal disease. However, FMT has not yet been approved as a general treatment due to safety issues. In addition, it has been reported that taking sufficient amounts of safe bacteria, including probiotics, can alleviate various immune diseases. However, beneficial microorganisms can vary depending on the patient's immune status. Some patients need to suppress an over-activated immune response (i.e., allergy or autoimmune disease), while some patients need to strengthen the immune system (i.e., cancer or viral infections). For example, when Th17-inducing probiotic bacteria *Bifidobacterium* were administered to a rheumatoid arthritis animal model, arthritis symptoms were aggravated (Tze Guan Tan, 113 (50): E8141-E8150, 2016). Therefore, it is of great therapeutic importance to identify beneficial microorganisms and to discover the mechanisms of effectors thereof.

Various hyperimmune diseases such as autoimmune and allergic diseases may be regulated by enhancement of Treg cells in vivo. In the present invention, *Bifidobacterium bifidum* PRI1 was selected as the best candidate by selecting probiotic candidate strains for the purpose of improving Treg cells induced by microorganisms which are stable. The ability of this bacterium to induce the production of dietary antigens or symbiotic induced regulatory T cells (iTreg cells) was identified using a germ free mouse (GF mouse) system. *Bifidobacterium bifidum* PRI1-derived effector molecules include butyrate, which is a metabolite, and acetate. In addition, according to the present invention, cell surface beta glucan/galactan polysaccharide (CSGG) derived from *Bifidobacterium bifidum* PRI1 functionally inhibits intestinal inflammation.

Accordingly, the present inventors have made extensive efforts to discover the mechanism of inducing Treg cells having therapeutic potential for immunomodulatory and inflammatory immune diseases, and as a result, the present inventors have found that the cell surface beta glucan/galactan polysaccharide (CSGG) of selected probiotic bacteria is a major effector molecule capable of inducing the production of iTreg cells, and confirmed that iTreg cells induced by the CSGG was able to inhibit colitis, thereby completing the present invention.

DISCLOSURE

Technical Problem

It is an object of the present invention to provide a polysaccharide comprising, as an active ingredient, β-1-6-glucan inducing regulatory T (Treg) cells and a probiotic strain producing the polysaccharide.

It is another object of the present invention to provide a composition for immunomodulation comprising the polysaccharide or the strain as an active ingredient.

It is a further object of the present invention to provide a pharmaceutical composition and food for the prevention, treatment, or alleviation of an immune disease or an inflammatory disease, which comprise the polysaccharide or the strain as an active ingredient.

It is a further object of the present invention to provide a method of preventing or treating an immune disease or an inflammatory disease, comprising administering a composition comprising the polysaccharide or the strain as an active ingredient.

It is a further object of the present invention to provide a use of a composition for the prevention or treatment of an immune disease or an inflammatory disease, the composition comprising the polysaccharide or the strain as an active ingredient.

It is a further object of the present invention to provide an immunosuppressant or immunotherapeutic agent comprising the polysaccharide or the strain as an active ingredient.

It is a further object of the present invention to provide a method of producing induced regulatory T (iTreg) cells using the polysaccharide or the strain.

It is a further object of the present invention to provide a cellular therapeutic agent for the prevention, treatment, or alleviation of an immune disease or an inflammatory disease, in which comprising induced regulatory T (iTreg) cells produced by the method as an active ingredient.

It is a further object of the present invention to provide a method of preventing or treating an immune disease or an inflammatory disease, comprising administering a cellular therapeutic agent comprising induced regulatory T cells (iTregs) produced by the method as an active ingredient.

It is a further object of the present invention to provide a use of a cellular therapeutic agent for the prevention or treatment of an immune disease or an inflammatory disease, wherein the cellular therapeutic agent comprises induced regulatory T cells (iTregs) produced by the method as an active ingredient.

Technical Solution

To achieve the above objects, the present invention provides a novel probiotic strain producing β-1-6-glucan.

The present invention also provides a polysaccharide comprising β-1-6-glucan as an active ingredient.

The present invention also provides a composition for immunomodulation comprising the polysaccharide or the strain as an active ingredient.

The present invention also provides a pharmaceutical composition and therapeutic agent for the prevention or treatment of an immune disease or an inflammatory disease, comprising the polysaccharide or the strain as an active ingredient.

The present invention also provides a food for the prevention or alleviation of an immune disease or an inflammatory disease, comprising the polysaccharide or the strain as an active ingredient.

The present invention also provides a method of preventing or treating an immune disease or an inflammatory disease, comprising administering a composition comprising the polysaccharide or the strain as an active ingredient.

The present invention also provides a use of a composition for the prevention or alleviation of an immune disease or an inflammatory disease, wherein the composition comprises the polysaccharide or the strain as an active ingredient.

The present invention also provides an immunosuppressant or immunotherapeutic agent comprising the polysaccharide or the strain as an active ingredient.

The present invention also provides a method of producing induced regulatory T (iTreg) cells comprising: treating dendritic cells (DCs) with the polysaccharide or the strain to obtain regulatory dendritic cells (rDCs); and co-culturing the rDCs with $CD4^+$ T cells to induce regulatory T (Treg) cells.

The present invention also provides a therapeutic agent for the prevention, treatment, or alleviation of an immune disease or an inflammatory disease, comprising induced regulatory T (iTreg) cells produced by the method as an active ingredient.

The present invention also provides a method of preventing or treating an immune disease or an inflammatory disease, comprising administering a cellular therapeutic agent comprising induced regulatory T (iTreg) cells produced by the method as an active ingredient.

The present invention also provides a use of a cellular therapeutic agent for the prevention or treatment of an immune disease or an inflammatory disease, wherein the cellular therapeutic agent comprises induced regulatory T (iTreg) cells produced by the method as an active ingredient.

BRIEF DESCRIPTION OF THE DRAWINGS

FIGS. 1A to 1C illustrate the flow cytometry and percentage analysis results of $CD4^+FOXP3^+$ cells, $CTLA4^+$, and $IL10^+$ in Treg cells of the colon of GF mice or the colon of mice colonized with Lpa or Bb (cLP). FIGS. 1D to 1F illustrate the absolute number of different types of Treg cells in the colon of GF mice colonized with bacteria and representative flow cytometry plots and signals. Numbers in the quadrants represent the percentage of cells, and circles in the graph plot represent individual mice corresponding to each parameter, data represent 3 to 5 independent experiments (n≥3 mice), and all graph plots show mean±SEM, and * $p<0.05$,  $p<0.01$, * $p<0.001$, **** $p<0.0001$ (Student's t test).

FIGS. 2A and 2B illustrate the proportion of representative IL-10/IL-12 cytokines (FIG. 2A) and Foxp3 expression (FIG. 2B) in the candidate probiotic strain *B. bifidum* PRI1 (Bb) selected as a bacteria strain promoting Treg induction, wherein each bacterial strain with the indicated colony-forming-unit (cfu) titers was incubated with total mesenteric lymph node (mLN) cells for 72 hours and then cytokine levels or Foxp3 expression were analyzed by ELISA or flow cytometry. FIG. 2C illustrates localization analysis of *B. bifidum* PRI1 (Bb) in the intestinal gap of GF mice through HISTO-FISH staining using a DNA-Cy5 probe (EUB338, red) 3 weeks after colonization. FIG. 2D illustrates cecum images (left) and cecum weights (right) of GF mice, Bb-monocolonized mice (Bb), and SPF mice. FIG. 2E illustrates the results of measuring the levels of butyrate and acetate in the cecum and feces of GF mice or Bb-monocolonized mice (Bb). FIG. 2F illustrates flow cytometry plots of CD4$^+$Foxp3$^+$ T cells in the colon (cLP) lamina propria of GF mice, mice colonized with SFB or Lpa, and SPF mice. Numbers in the quadrants represent the percentage of cells, circles in the graph plot represent individual mice corresponding to each parameter, data represent 3 to 5 independent experiments (n≥3 mice) (*B. bifidum*: Bb, *Lactobacillus acidophilus*: Lac, *Lactobacillus casei*: Lca, *Lactobacillus reuteri*: Lre, *Lactobacillus paracasei*: Lpa, Segmented filamentous bacteria: SFB), and all graph plots show mean±SEM, and * $p<0.05$,  $p<0.01$, * $p<0.001$ (Student's t test).

FIG. 3A illustrates the frequency of CD4$^+$Foxp3$^+$ T cells in the small intestinal lamina propria (siLP), mLN, pLN, and spleen of SPF mice, GF mice, or mice monocolonized with Bb, SFB, or Lpa. FIGS. 3B and 3C illustrate flow cytometry plots and frequencies of CD4$^+$CD103$^+$Foxp3$^+$ (FIG. 3B) and CD4$^+$CD44$^{hi}$CD62$^{lo}$Foxp3$^+$ T cells (FIG. 3C) in cLP or siLP of mice monocolonized with respective bacteria, wherein the plots and frequencies were expressed as percentages. Numbers in the quadrants represent the percentage of cells, circles in the graph plot represent individual mice corresponding to each parameter, data represent 3 to 5 independent experiments (n≥3 mice), and all graph plots show mean±SEM, and * $p<0.05$, ** $p<0.01$ (Student's t test).

FIGS. 4A and 4B illustrate the frequency of the Helios$^-$ and Nrp1$^-$ Treg populations in the indicated lymphoid tissues. FIGS. 4C and 4D illustrate the flow cytometry plots and frequencies of Helios$^-$Foxp3$^+$ cells (FIG. 4C) or RORγt$^+$ Helios$^-$Foxp3$^+$ Treg cells (FIG. 4D) from indicated organs of GF mice or mice monocolonized with Bb or Lpa, wherein the plots and frequencies were expressed as a percentage. Numbers in the quadrants represent the percentage of cells, circles in the graph plot represent individual mice corresponding to each parameter, data represent 3 to 5 independent experiments (n≥3 mice), and all graph plots show mean±SEM, and * $p<0.05$, ** $p<0.01$ (Student's t test).

FIG. 5A illustrates an experimental strategy for the analysis of new production of pTreg cells after monocolonization with Bb. FIGS. 5B and 5C illustrate the results obtained after transferring naive CD4$^+$Foxp3$^-$ T cells sorted from CD45.1$^+$Foxp3$^{GFP}$ reporter mice into GF mice and monocolonizing the mice with Bb for 3 weeks, the Foxp3$^+$ Treg populations being analyzed by GFP expression in cLP (FIG. 5B) and siLP (FIG. 5C). FIG. 5D illustrates the results of measuring the frequencies of Foxp3$^+$ Treg populations by GFP expression in indicated lymphoid organs. FIG. 5E illustrates the results of analyzing Foxp3$^+$ Treg cells in cLP after transferring naive CD4$^+$Foxp3$^-$ T cells sorted from CD45.1$^+$Foxp3$^{GFP}$ reporter mice into SPF mice and feeding the mice with mock (PBS) or Bb ($5\times10^8$ cfu) every other day for 3 weeks. Data represent 3 to 5 independent experiments (n≥3 mice), and all graph plots show mean±SEM, and * $p<0.05$, ** $p<0.01$ (Student's t test).

FIGS. 6A and 6B illustrate the results of analyzing cLP CD4$^+$Foxp3$^+$ populations of donor (Thy1$^+$OT-II) cells after adopting CTV-labeled naive CD4$^+$OT-II$^+$Foxp3$^-$ T cells of Thy1.1$^+$Foxp3$^{GFP}$ mice to GF mice or GF mice pre-colonized for 14 days and then feeding the mice with OVA (20 mg) every other days for 7 days, FIGS. 6A and 6B illustrate FACS plots and the frequency of Treg cells produced in vivo, respectively. FIGS. 6C to 6E illustrate the results of measuring and analyzing body weight, colon length, and changes in histopathology (C, D, and E, respectively) after adopting naive CD4$^+$CBir$^+$Foxp3$^-$ T cells sorted from CBir$^{Tg}$CD45.1$^+$Foxp3$^{GFP}$ mice to SPF Rag1$^{-/-}$ recipients, and then being fed with Bb or PBS every day until the end of the experiment. FIGS. 6F to 6G illustrate flow cytometry plots and frequencies of CBir$^+$CD45.1$^+$Foxp3$^+$ Treg cells (FIG. 6F) and IFN-γ$^+$ cells (FIG. 6G) in cLP of mock or Bb-colonized mice. FIG. 6H illustrates the results of analyzing relative proliferation of Treg cells responding to the indicated antigens by FACS 3 days after sorting CD4$^+$ cells of GF or Bb-GF mice and labeling the cells with CTV, and then culturing the cells together with spleen APC from which T cells have been removed, in the presence of fecal antigens of GF mice and Bb- or Lpa-colonized mice. FIG. 6I illustrates the results of comparing the frequency distribution of 43 intrinsic α chains and 61 intrinsic @chains of the TCR-CDR3 region in Treg of colon, mLN, and spleen of Bb-monocolonized mice compared with GF mice. Numbers in the quadrants represent the percentage of cells, circles in the graph plot represent individual mice corresponding to each parameter, data represent 3 to 5 independent experiments (n≥3 mice), and all bar graphs show mean±SEM, and * $p<0.05$,  $p<0.01$, * $p<0.001$ (Student's t test).

FIG. 7A illustrates an experimental strategy for determining OVA$^-$ specific pTreg cells induced in response to dietary antigens (OVA-specific OTII T cells) in GF mice or Bb-colonized GF mice. FIG. 7B illustrates an experimental strategy for determining microbiota (flagellin-specific CBir T cells)-specific pTreg cells derived from Rag1$^{-/-}$ SPF mice fed with PBS or Bb. FIG. 7C illustrates RORγ, GATA3, and T-bet population analysis of CD4$^+$Foxp3$^-$ or CD4$^+$Foxp3$^+$ T cells in cLP of Rag1$^{-/-}$ SPF mice to which CBir naive T cells fed with PBS or Bb were transferred. FIG. 7D illustrates an experimental strategy for determining Bb-induced Treg proliferation in the presence of a combination of fecal antigens of mice monocolonized with Bb or Lpa or GF mice. FIG. 7E illustrates the results of analyzing relative proliferation of Treg cells responding to the indicated antigens by FACS 3 days after screening all colon CD4$^+$ cells of GF mice or mice monocolonized with Bb, and labeling the cells with CTV, and then culturing the cells together with spleen cells (APCs) from which T cells have been removed, in the presence of a combination of fecal antigens of GF or mice monocolonized with Bb or Lpa. Data represents 3 independent experiments (n≥3 mice), and all graph plots show mean±SEM, and * $p<0.05$, ** $p<0.01$ (Student's t test).

FIG. 8A illustrates the results of comparing Shannon diversity in a and β chains of Treg cell repertoires obtained from different organs (colon, MLN, and spleen) of GF mice or Bb-monocolonized mice. FIG. 8B illustrates heat maps of a and @chains showing the frequency of top 85 TCR-CDR3 regions in colon Treg cells of Bb-monocolonized mice and GF mice, the CDR3 region of the 'common' marker (28 peptides) indicates the presence of read counts in each group, the hue indicates the relative frequency at which the given TCR was found. FIG. 8C illustrates the frequency distribution of a typical TCR-CDR3 alpha region represented by a bidirectional bar plot: 85 in the large intestine, 1469 in the MLN, and 1381 in the spleen, and FIG. 8D illustrates the frequency distribution of a typical TCR-CDR3 beta region represented by a bidirectional bar plot: 118 in the colon, 1724 in the MLN, and 1381 in the spleen.

FIG. 9A illustrates the structure of cell surface β-1,6-glucan (CSGG) polysaccharide of *B. bifidum*; Glcp: glucopyranose. FIG. 9B illustrates effect of β-1,6-glucan treatment on CSGG-induced iTreg cells. FIG. 9C illustrates the population and phenotype of Treg cells in GF mice or GF mice colonized with Bb or Lpa or subjected to intraperitoneal injection of CSGG (100 µg/dose) every other day for 3 weeks. FIG. 9D illustrates the results of confirming the induction of dose-dependent human CD4$^+$CD25$^+$Foxp3$^+$ Tregs by co-culture of DC pretreated with CSGG together with naive CD4$^+$ T cells of PBMCs of healthy donors. FIG. 9E illustrates the analysis of RNA-Seq of mock- or CSGG-treated CD11c$^+$ DCs. FIG. 9F illustrates the results obtained by culture of naive CD4$^+$ T cells derived from mock- or CSGG-pretreated mice and CD11c$^+$ DCs together with suboptimal iTreg products wherein the population of CD4$^+$Foxp3$^+$ Treg cells was determined by flow cytometry. FIG. 9G illustrates the results of measuring TGFβ1 levels in culture supernatants obtained after culturing naive CD4$^+$ T cells together with wild-type or TLR2-deficient CD11c$^+$ DCs pretreated with mock or CSGG. Data represents at least 3 independent experiments, and all bar graphs show mean±SEM, and * p<0.05,  p<0.01, * p<0.001 (Student's t test).

FIG. 10A illustrates the results of quantifying the relative mRNA expression of normalized cytokines against Hprt in the entire colon of GF mice or Bb-monocolonized mice. FIGS. 10B to 10D illustrate relative mRNA expression levels of cLP-DCs (MHCII$^+$CD11c$^+$CD11b$^+$CD103$^+$F4/80$^-$) of GF mice or Bb-monocolonized mice. FIG. 10E illustrates an experimental strategy for Treg induction in vitro in a DC:T co-culture system. FIG. 10F illustrates the dose-dependent induction of Foxp3$^+$ cells and survival of T cells in response to splenic CD11c$^+$DCs and various amounts of Bb (cfu) titration. FIG. 10G illustrates the results of analyzing Foxp3$^+$ Treg cells in live cells after co-culture of Bb- or Lpa-pretreated splenic CD11c$^+$DCs together with naive CD4$^+$ T cells for 3 days under suboptimal Treg induction conditions (anti-CD3; 0.1 µg/ml, TGF-β; 0.1 ng/ml, IL-2; 100 unit/ml), IL-10 secretion was determined by ELISA analysis of the culture supernatant. Data represent 3 to 5 independent experiments (n≥3 mice), all graph plots show mean±SEM, * p<0.05, ** p<0.01 (Student's t test), and representative flow cytometry and mean frequency of CD4$^+$Foxp3$^+$ Treg cells are shown.

FIG. 11A illustrates the results of analyzing Foxp3$^+$ Treg cells by FACS 3 days after co-culture of splenic CD11c$^+$DCs pretreated with a fraction of *B. bifidum* together with naive CD4$^+$ T cells under suboptimal Treg induction conditions. FIG. 11B illustrates the results of analyzing Foxp3$^+$ Treg cells by FACS 3 days after co-culture of splenic CD11c$^+$DCs pretreated with the indicated amounts of total cell surface polysaccharides (tCSPS) together with naive CD4$^+$ T cells. FIG. 11C illustrates the structure of neutral (CSGG) or negatively charged polysaccharides (PGβG) isolated from total cell surface polysaccharides (tCSPS) of *B. bifidum* (Glcp: glucopyranose, Galp: galactopyranose, Galf: glucofuranose, Gro: glycerol, n=repeat units, the relative abundance of each polysaccharide indicated by % (mol/mol)). FIG. 11D illustrates the results of comparing CD4$^+$Foxp3$^+$ Treg induction activity between neutral (CSGG; 5 µg/ml) and negatively charged polysaccharide (PGRG: 100 µg/ml) compared to tCSPS (100 µg/ml). FIG. 11E illustrates the effect of β-1,6-glucanase, β-1,4-galactanase, and β-1,4-glucanase treatment on the induction of CSGG-induced iTreg cells (CSGG; 50 µg/ml). FIG. 11F illustrates the results obtained after treating naive CD4$^+$ T cells with DCs-free CSGG (50 µg/ml) under suboptimal Treg induction conditions (anti-CD3; 0.1 µg/ml, α-CD28; 0.1 µg/ml, TGF-β; 0.1 ng/ml, IL-2; 100 unit/ml). Data represent 3 to 5 independent experiments (n≥3 mice), and all graph plots show mean±SEM, and * p<0.05, ** p<0.01 (Student's t test);

FIG. 12A illustrates the production of CD4$^+$Foxp3$^+$ populations in vitro after co-culture of naive CD4$^+$ T cells together with CD11c$^+$ DCs pretreated with bacteria or CSGG under suboptimal Treg induction conditions. FIG. 12B illustrates CD4$^+$Foxp3$^+$ populations in GF mice or mice monocolonized by intraperitoneally injecting Bb, Lpa, or CSGG (100 µg/dose) into GF mice every other day for 3 weeks. FIGS. 12C and 12D illustrate the results of analyzing the frequency of indicated populations of Treg cells in lymphoid organs, after intraperitoneally injecting CSGG (100 µg/dose) or PBS into GF mice every other day for 3 weeks. Data represent 3 to 5 independent experiments (n≥3 mice), and all graph plots show mean±SEM, and * p<0.05,  p<0.01, * p<0.001 (Student's t test).

FIG. 13A illustrates the results of confirming cytokine levels in culture supernatants obtained after co-culture of mock- or CSGG-pretreated CD11c$^+$ DCs and naive CD4$^+$ T cells. FIG. 13B illustrates the effect of anti-TGFβ Ab treatment on in vitro CD4$^+$Foxp3$^+$ Treg induction after Bb or CSGG treatment. FIG. 13C illustrates the results of measuring iTreg induction 3 days after co-culture of CSGG-pretreated IL-10$^{-/-}$ KO mice or wild-type CD11c$^+$ DCs with wild-type naive CD4$^+$ T cells. FIG. 13D illustrates the results of analyzing RNA-seq data to determine the expression of genes encoding TLR subtypes upon CSGG treatment. FIG. 13E illustrates the results of measuring CD4$^+$Foxp3$^+$ Treg cell induction by flow cytometry after co-culture of naive CD4$^+$ T cells and mock- or CSGG-pretreated mice-derived CD11c$^+$ DCs for 3 days under suboptimal iTreg production conditions. FIG. 13F illustrates the results of measuring the levels of IL-10 and IFNγ cytokines in culture supernatants after co-culture of wild-type CD11c$^+$ DCs or mock- or CSGG-pretreated TLR2-deficient CD11c$^+$ DCs with naive CD4$^+$ T cells. FIG. 13G illustrates the results of examining iTreg induction by flow cytometry after pretreating CD11c$^+$ DCs with mock or CSGG in the presence of blocking antibodies against C-type lectins and then co-culturing the cells together with naive CD4+ T cells. FIG. 13H illustrates the results of measuring iTreg induction 3 days after co-culture of CD11c+ DCs of wild-type or CSGG-pretreated Dectin1−/− or Dectin2−/− KO mice together with naive CD4+ T cells. Data represents at least 3 independent experiments, and all bar graphs show mean±SEM, and * p<0.05 (Student's t test).

FIGS. 14A to 14C illustrate the results obtained after adopting and co-transferring naive CD4+Foxp3− T cells isolated from Thy1.1+Foxp3$^{GFP}$ reporter mice to RAG1−/− recipients in the indicated combination of iTreg cells, wherein body weight, colon length, and pathological changes in colon tissue were measured. FIG. 14D illustrates the results of analyzing Foxp3 stability of Treg cells transferred from cLP at the end of the experiment wherein the purity of CD4+Foxp3$^{GFP+}$ cells sorted upon transfer was 98% or greater. FIGS. 14E to 14G illustrate the results obtained after adoptive transfer of CD4+Foxp3− T cells isolated from CD45.1+Foxp3$^{GFP}$ reporter mice into RAG1−/− mice, and then intraperitoneally administering PBS or CSGG (100 μg/ml) thereto, wherein body weight, colon length, and pathological changes in colon tissue were measured. FIG. 14H illustrates the results of analyzing the IFNγ production of effector T cells in cLP at the end of the experiment. Data represents at least 3 independent experiments, and all bar graphs show mean±SEM, and * p<0.05,  p<0.01, * p<0.001, **** p<0.0001 (Student's t test).

FIG. 15A illustrates the results obtained after sorting and co-culture of CTV-labeled naive responder Thy1.1+CD4+Foxp3− T cells, wherein CD45.1+CD4+Foxp3+ iTreg cells were generated in vitro as purified mock- or CSGG-treated APCs from splenocytes from which T cells of labeled CD45.2+ mice were removed, and the proliferation of responder T cells was analyzed by flow cytometry. FIG. 15B illustrates the colon length of adoptive transfer RAG1−/− colitis inhibited by nTreg and iTreg cells induced in vitro by mock, Bb, or CSGG. FIG. 15C illustrates the colon length of RAG1−/− colitis induced by naive T cells adopted via intraperitoneal administration of mock (PBS) or CSGG (100 μg/dose). FIG. 15D illustrates CD4+CD45.1+Foxp3+ Treg populations in mLN of mock- or CSGG-treated adoptively transferred RAG1−/− mice. Data represents at least 2 independent experiments, and all bar graphs show mean±SEM, and * p<0.05 (Student's t test).

DETAILED DESCRIPTION AND EXEMPLARY EMBODIMENTS

Figure 1:
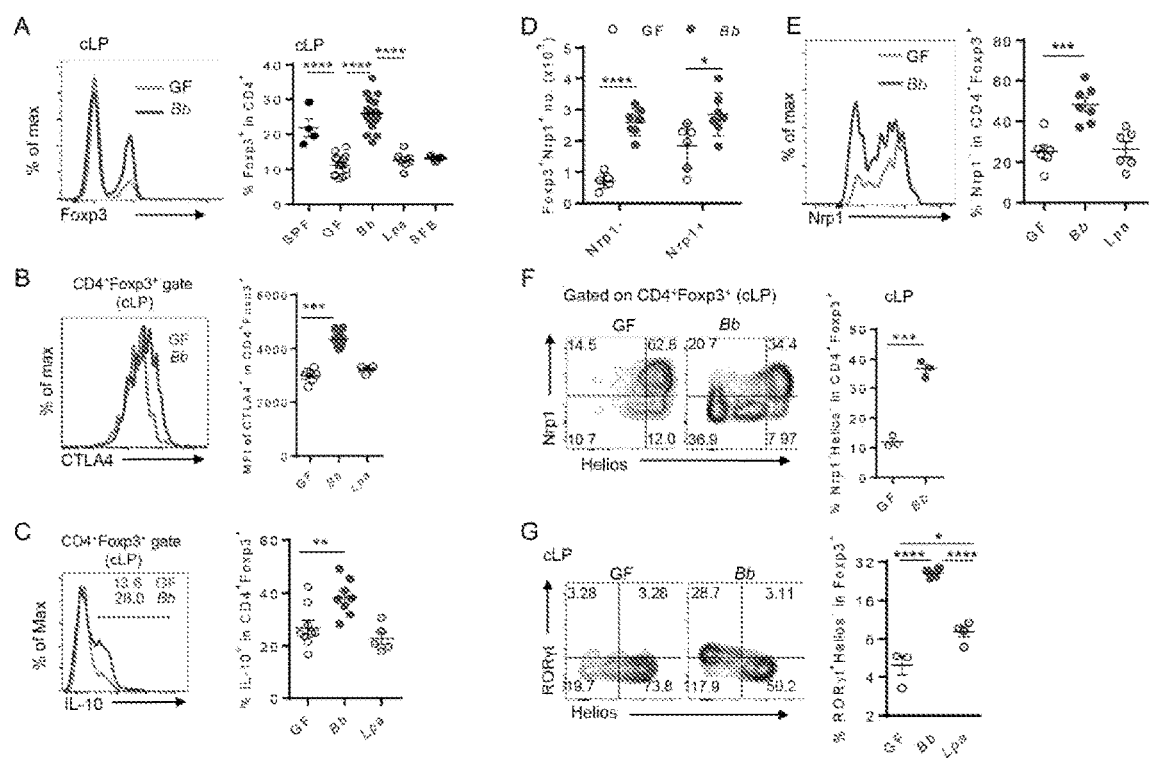
FIG. 1 illustrates an increase of the Treg population in the colonic lamina propria caused by *B. bifidum* monocolonization.

Unless defined otherwise, all technical and scientific terms used herein have the same meanings as commonly understood by one of ordinary skill in the art to which the present invention pertains. In general, the nomenclature used herein is well known and commonly used in the art.

The present invention shows that human symbiotic bacterium *Bifidobacterium bifidum* PRI1 (*B. bifidum*) is able to enhance the differentiation of naive CD4 T cells into functionally active Foxp3+ iTreg cells that inhibit inflammatory colitis. Cell-surface-derived beta-glucan/galactan polysaccharide (CSGG) is an active molecule that summarizes the function of the entire bacteria when inducing iTreg cells. The mechanism of action of CSGG is mediated by the induction of the TLR2/IL-10 regulatory pathway in dendritic cells (DCs).

Since dysregulation of symbiotic microorganisms is closely related to the development of many diseases, the promotion of Treg cells in vivo by Treg-inducing microorganisms may enable the control of various inflammatory diseases. Intestinal microorganisms play an important role in maintaining immune homeostasis, and this dysregulation of intestinal microorganisms may cause inflammatory diseases associated with impaired function of immunosuppressive Foxp3+ T regulatory (Treg) cells. Although some symbiotic microorganisms are known to enhance the induction of Treg cells (Tanoue, T et al., *Nature reviews Immunology* 16: 295-309, 2016), the "effector molecules" that control this process, i.e., molecular mechanism of Treg cells induced by bacteria, antigen specificity, and target cells, are not yet known.

Therefore, in the present invention, probiotic candidate strains that are generally regarded as safe (GRAS) were selected, and *Bifidobacterium bifidum* PRI1 (*B. bifidum*), having various TCR specificities against dietary antigens or symbiotic bacteria, was selected as the best candidate of Treg-inducing bacteria. *Bifidobacterium bifidum* PRI1 was deposited on May 19, 2017 at the Korean Collection for Type Cultures (Accession Number: KCTC13270BP). In addition, it was confirmed that *B. bifidum* and cell-surface-derived beta-glucan/galactan polysaccharide (CSGG) thereof were major components that induce Treg, and in particular, CSGG efficiently reproduces the activity of whole bacteria and partially mediates regulatory dendritic cells through a TLR2-dependent mechanism and acts both in mice and humans, thereby inducing Treg cells. Treg cells induced by *B. bifidum* or induced by purified CSGG, showed stable and potent therapeutic or inhibitory capacity for colitis.

Therefore, the present invention relates to a novel strain producing β-1-6-glucan.

In addition, in one aspect, the present invention is directed to a polysaccharide comprising β-1-6-glucan as an active ingredient.

In the present invention, the polysaccharide may further comprise β-1-4-galactan, β-1-6-galactan, or D-galactofuranan, and these polysaccharides may be used alone. In particular, the polysaccharide may be a composite having β-1-6-glucan as a main component or a single substance.

In addition, the β-1-6-glucan, β-1-4-galactan, β-1-6-galactan, and D-galactofuranan may be included in a molar ratio of 5-50:2-15:2-15:1-5, more preferably in a molar ratio of 10-20:3-10:3-10:2-4, and most preferably in a molar ratio of 18:5:5:2, with respect to total polysaccharides, but the present invention is not limited thereto. The polysaccharides may include 5-50 wt % of β-1-6-glucan, 2-15 wt % of β-1-4-galactan, 2-15 wt % of β-1-6-galactan, and 1-5 wt % of β-galactofuranan with respect to a total of 100 wt %. Preferably, the polysaccharides may include 10-20 wt % of β-1-6-glucan, 3-wt % of β-1-4-galactan, 3-10 wt % of β-1-6-galactan, and 2-4 wt % of β-galactofuranan with respect to a total of 100 wt %, and each polysaccharide may be included in an amount of 18 wt %, 5 wt %, 5 wt %, and 2 wt % with respect to a total of 100 wt %.

In the present invention, the polysaccharide preferably has a molecular weight of about 3-5 kDa, more preferably 4 kDa, but is not limited thereto, as long as it is any mixture having various molecular weights of 100 kDa or less.

In the present invention, the charge of the polysaccharide may be neutral.

In the present invention, the polysaccharide may induce regulatory T (Treg) cells, and the regulatory T (Treg) cells are preferably CD4$^+$Foxp3$^+$ Treg cells, but are not limited thereto.

Induction of the regulatory T (Treg) cells may be mediated by dendritic cells (DCs). In addition, the regulatory T cells (Tregs) may increase the induction of IL-10 and TGF-β production.

In the present invention, the polysaccharide is preferably derived from a *Bifidobacterium bifidum* strain, is more preferably derived from a strain having a base sequence with at least 99% homology to *Bifidobacterium bifidum* PRI1, and is most preferably derived from a *Bifidobacterium bifidum* PRI1 (KCTC 13279BP) strain, but is not limited thereto.

In the present invention, the strain having a base sequence with at least 99% homology to *Bifidobacterium bifidum* PRI1 may be *Bifidobacterium bifidum* A8 or *Bifidobacterium bifidum* LMG11582.

In the present invention, the polysaccharide preferably has anti-inflammatory or immune-function-modulating activity, and more preferably immunosuppressive activity, but is not limited thereto. People with intestinal wounds such as intestinal bleeding and the like may have side effects if they take probiotics incorrectly, and in such cases, therapeutic effects may be obtained when polysaccharides are administered.

In another aspect, the present invention is directed to a strain producing β-1-6-glucan polysaccharide.

In the present invention, the strain is preferably *Bifidobacterium bifidum*, but is not limited thereto, as long as the strain produces CSGG polysaccharide. In addition, in the present invention, the *Bifidobacterium bifidum* preferably has a base sequence with at least 99% homology to *Bifidobacterium bifidum* PRI1, and is more preferably *Bifidobacterium bifidum* PRI1 (KCTC13279BP), but is not limited thereto.

In the present invention, the strain may further produce β-1-4-galactan, β-1-6-galactan, or β-galactofuranan, but is not limited thereto.

In the present invention, the strain may induce regulatory T cells (Tregs), and the regulatory T (Treg) cells may preferably be CD4$^+$Foxp3$^+$ Treg cells, but is not limited thereto. In addition, the strain may increase the induction of IL-10 and TGF-β production.

The induction of regulatory T (Treg) cells may be mediated by DCs.

In the present invention, the strain preferably has anti-inflammatory or immune-function-modulating activity, and more preferably has activity of inhibiting hyperimmunity, but is not limited thereto.

In particular, the strain produces CSGG polysaccharides, and thus induces antigen-specific Tregs by various antigens such as food, other intestinal bacteria, or bacteria-derived substances, and therefore may be applied to the treatment of inflammation or immune diseases.

In another aspect, the present invention is directed to a composition for immunomodulation comprising, as an active ingredient, β-1-6-glucan polysaccharide or a *Bifidobacterium bifidum* strain producing the polysaccharide.

In the present invention, the polysaccharide may further comprise β-1-4-galactan, β-1-6-galactan, or D-galactofuranan, but is not limited thereto.

In the present invention, the polysaccharide or the strain may induce regulatory T (Treg) cells, and the regulatory T (Treg) cells are preferably CD4$^+$Foxp3$^+$ Treg cells, but are not limited thereto. In addition, the polysaccharide or the strain may increase the induction of IL-10 and TGF-β production.

The induction of regulatory T (Treg) cells may be mediated by DCs.

As used herein, the term "immunomodulation" means relieving immune imbalance in the blood and maintaining immune homeostasis. Maintaining immune homeostasis refers to a condition in which immune tolerance which is a mechanism for inhibiting immunity, and immunity which promotes immune response, are balanced, and the maintenance of such a condition is an essential factor in the treatment of immune diseases, especially autoimmune diseases.

In another aspect, the present invention is directed to an immunosuppressant or an immunotherapeutic agent comprising, as an active ingredient, β-1-6-glucan polysaccharide or a *Bifidobacterium bifidum* strain producing the polysaccharide.

The term "immunosuppressant" as used herein refers to various substances used to reduce or block the ability of a host to produce antibodies (humoral immune response) or the ability to elicit a cellular immune response to the action of an antigen.

In addition, the term "immunotherapy" of the present invention refers to a treatment for defeating a disease by inducing an activation or suppression response of the body's immune system. The most representative immunotherapy is cancer immunotherapy, which induces immune activity and kills cancer cells, and immune treatment through immunosuppressants is possible for diseases such as autoimmune disease, inflammatory bowel disease (IBD), and allergies, which are diseases induced by abnormal immune responses.

Therefore, in the present invention, "immunosuppressant" and "immunotherapeutic agent" may be used in the same meaning.

In another aspect, the present invention is directed to a pharmaceutical composition for the prevention or treatment of an immune disease or an inflammatory disease, which comprises, as an active ingredient, β-1-6-glucan polysaccharide or a *Bifidobacterium bifidum* strain producing the polysaccharide.

In the present invention, the polysaccharide may further comprise β-1-4-galactan, β-1-6-galactan, or D-galactofuranan, but is not limited thereto.

In the present invention, the polysaccharide or the strain may induce regulatory T (Treg) cells, and the regulatory T (Treg) cells are preferably CD4$^+$Foxp3$^+$ Treg cells, but is not limited thereto. In addition, the polysaccharide or the strain may increase the induction of IL-10 and TGF-β production.

The induction of regulatory T (Treg) cells may be mediated by DCs.

In addition, the immunomodulatory composition may be used as a pharmaceutical composition or health functional food for the purpose of regulating immune activity and preventing, improving or treating immune diseases. In this regard, the amount and form thereof may be appropriately adjusted according to the purpose of use.

The composition for immunomodulation may exhibit an immunostimulating effect and a hyperimmunosuppressive effect. The immunostimulating effect is an effect of increasing the expression of TNF-α in macrophages or enhancing the proliferative capacity of splenocytes to promote immunity. The hyperimmunosuppressive effect is an effect of suppressing hyperimmunity by inhibiting lymphocyte overexpression caused by a nonspecific stimulator in splenocytes.

The "immune disease" to be prevented or treated by the composition according to the present invention may be any one selected from the group consisting of dermatitis, allergies, rhinitis, gout, ankylosing spondylitis, rheumatic fever, lupus, fibromyalgia, peritendinitis, Type 1 diabetes, scleroderma, neurodegenerative disease, Type 2 diabetes, silicosis, atherosclerosis, vitiligo, conjunctivitis, and autoimmune diseases, but is not limited thereto.

The "autoimmune disease" to be prevented or treated by the composition according to the present invention may be any one selected from the group consisting of rheumatoid arthritis, systemic scleroderma, atopic dermatitis, psoriasis, asthma, Guilian-Barre syndrome, myasthenia gravis, dermatomyositis, polymyositis, multiple sclerosis, autoimmune encephalomyelitis, nodular polyarteritis nodosa, temporal arteritis, childhood diabetes, alopecia areata, pemphigus, aphthous stomatitis, Crohn's disease, and Behcet's disease, but is not limited thereto.

The "inflammatory disease" to be prevented or treated by the composition according to the present invention refers collectively to diseases of which inflammation is a main lesion, and may be any one selected from the group consisting of swelling, allergies, asthma, conjunctivitis, periodontitis, rhinitis, tympanitis, sore throat, tonsillitis, pneumonia, gastric ulcer, gastritis, Crohn's disease, colitis, hemorrhoids, gout, ankylosing spondylitis, rheumatic fever, lupus, fibromyalgia, psoriatic arthritis, osteoarthritis, rheumatoid arthritis, periarthritis, tendinitis, tenosynovitis, myositis, hepatitis, cystitis, nephritis, Sjogren's syndrome, myasthenia gravis, and multiple sclerosis, but is not limited thereto.

The term "prevention" as used herein means all actions that inhibit or delay the onset of an immune disease or an inflammatory disease via administration of a pharmaceutical composition according to the present invention.

The term "treatment" as used herein means all actions that improve or beneficially change symptoms of an immune disease or an inflammatory disease via administration of a pharmaceutical composition according to the present invention.

The pharmaceutical composition according to the present invention exhibits the immunostimulating effect of the active ingredient, or a preventive or therapeutic and anti-inflammatory effect on various immune diseases through a hyperimmunosuppresive effect.

The pharmaceutical composition may further include suitable carriers, excipients, and diluents commonly used in pharmaceutical compositions, in addition to β-1-6-glucan, β-1-4-galactan, β-1-6-galactan and β-galactofuranan (CSGG) polysaccharides or a *Bifidobacterium bifidum* strain producing the polysaccharides as an active ingredient.

Carriers, excipients and diluents which may be included in the composition include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, mineral oil, and the like. In formulating the composition, diluents or excipients such as fillers, extenders, binders, wetting agents, disintegrating agents, and surfactants are usually used.

The pharmaceutical composition according to the present invention may be used by formulating the same into various forms according to general methods. Suitable formulations include oral preparations such as tablets, pills, powders, granules, sugar-coated tablets, hard or soft capsules, solutions, suspensions or emulsions, injections, aerosols, and the like, external preparations, suppositories, and sterile injectable solutions, but are not limited thereto.

The pharmaceutical compositions according to the present invention may be prepared into a suitable formulation using a pharmaceutically inert organic or inorganic carrier. That is, when the formulation is in the form of tablets, coated tablets, sugar-coated tablets, and hard capsules, the organic or inorganic carrier may include lactose, sucrose, starch or a derivative thereof, talc, calcium carbonate, gelatin, or stearic acid or a salt thereof. In addition, when the formulation is in the form of soft capsules, the organic or inorganic carrier may include vegetable oil, wax, fat, and semisolid and liquid polyol. In addition, when the formulation is in the form of a solution or syrup, the organic or inorganic carrier may include water, polyol, glycerol, vegetable oil, and the like.

The pharmaceutical composition according to the present invention may further include, in addition to the above-described carriers, a preservative, a stabilizer, a wetting agent, an emulsifier, a solubilizing agent, a sweetener, a colorant, an osmotic pressure control agent, an antioxidant, and the like.

The pharmaceutical composition according to the present invention is administered in a pharmaceutically effective amount. The term "pharmaceutically effective amount" as used herein refers to an amount sufficient to treat diseases at a reasonable benefit/risk ratio applicable to medical treatment, and an effective dosage level may be determined according to factors including the type of disease of patients, the severity of disease, the activity of drugs, sensitivity to drugs, administration time, administration routes, excretion rate, treatment period, and co-administered drugs, and other factors well known in the medical field. The pharmaceutical composition according to the present invention may be administered as an individual therapeutic agent or in combination with other therapeutic agents, may be administered sequentially or simultaneously with conventional therapeutic agents, and may be administered in a single dose or multiple doses. It is important to administer the pharmaceutical composition in the minimum amount that maximizes effects without side effects in consideration of all the above-described factors, which may be easily determined by those of ordinary skill in the art.

The compositions according to the present invention may be administered in combination with immune-related proteins, in particular autoimmune- or allergy-related proteins. Specific examples of the proteins include autoantigens involved in autoimmune diseases. For example, the proteins may include autoantigens involved in rheumatoid arthritis, such as heat-shock proteins (HSPs), citrullinated filaggrin, glucose-6-phosphate isomerase, p205, collagen, and the like; autoantigens involved in Type I diabetes, such as insulin, Zinc transporter 8 protein (ZnT8), Pancreatic and duodenal homeobox 1 (PDX1), Chromogranin A (CHGA), and Islet amyloid polypeptide (IAPP); and autoantigens involved in myasthenia gravis, such as an acetylcholine receptor. In addition to all types of autoantigens known in autoimmune diseases, the proteins may include various allergens known to cause food allergies, such as peanuts, milk, eggs, tree nuts, beans, crustaceans such as shrimp and the like, fish-derived substances, and the like.

The pharmaceutical composition of the present invention may be administered to a subject via various routes. The pharmaceutical composition may be administered via, for example, subcutaneous injection, intravenous injection, intramuscular injection, intrauterine epidural injection, or intracerebroventricular injection. The pharmaceutical composition of the present invention is determined according to the type of drug which is the active ingredient, along with various related factors such as the disease to be treated, the administration route, the age, gender, and body weight of the patient, the severity of the disease, and the like.

The administration method of the pharmaceutical composition according to the present invention may be easily selected according to the dosage form, and the pharmaceutical composition may be administered orally or parenterally. The dosage may vary depending on the age, gender, and body weight of the patient, the severity of the disease, and the administration route.

In another aspect, the present invention is directed to a therapeutic agent for the prevention or treatment of an immune disease or an inflammatory disease, which comprises, as an active ingredient, β-1-6-glucan polysaccharide or a *Bifidobacterium bifidum* strain producing the polysaccharide.

In another aspect, the present invention is directed to a method of preventing or treating an immune disease or an inflammatory disease comprising administering a composition comprising β-1-6-glucan polysaccharide or a *Bifidobacterium bifidum* strain producing the polysaccharide as an active ingredient.

In the present invention, the polysaccharide may further comprise β-1-4-galactan, β-1-6-galactan, or D-galactofuranan.

In another aspect, the present invention is directed to a use of a composition for the prevention or treatment of an immune disease or an inflammatory disease, wherein the composition comprising β-1-6-glucan polysaccharide or a *Bifidobacterium bifidum* strain producing the polysaccharide as an active ingredient.

In the present invention, the polysaccharide may further comprise β-1-4-galactan, β-1-6-galactan, or D-galactofuranan.

The pharmaceutical composition according to the present invention not only provides excellent immunity enhancement and hyperimmunosuppressive effects, but also has low toxicity and side effects due thereto, so the pharmaceutical composition can be used safely even for long-term administration for the purpose of treating or preventing immune diseases.

*B. bifidum* or CSGG according to the present invention may induce a variety of antigen-specific Treg cells in vivo, and thus may be used as an oral resistance adjuvant.

In another aspect, the present invention is directed to a food for the prevention or alleviation of an immune disease or an inflammatory disease, which comprises β-1-6-glucan polysaccharide or a *Bifidobacterium bifidum* strain producing the polysaccharide as an active ingredient.

In the present invention, the polysaccharide may further produce β-1-4-galactan, β-1-6-galactan, or D-galactofuranan, but is not limited thereto.

The food for the prevention or alleviation of an immune disease or an inflammatory disease may be a health functional food having activity of maintaining homeostasis of an immune function by enhancing immune activity or suppressing or alleviating hyperimmunity.

In the present invention, the polysaccharide or the strain may induce regulatory T (Treg) cells, and the regulatory T (Treg) cells may preferably be CD4$^+$Foxp3$^+$ Treg cells, but are not limited thereto.

The induction of regulatory T (Treg) cells may be mediated by DCs, and may induce the production of IL-10 and TGF-IL-10 and TGF-β.

The term "food" as used herein includes all foods in the general sense, such as meat, sausages, bread, chocolates, candies, snacks, confectioneries, pizza, ramen, other noodles, gum, dairy products including ice cream, various soups, beverages, tea, drinks, alcoholic beverages, vitamin complexes, health functional foods, health foods, and the like.

The term "health functional food" has the same meaning as "food for special health use (FoSHU)", and means a food processed to efficiently exhibit bioregulation in addition to nutritional supply and having excellent pharmaceutical and medical effects. The term "functionality" as used herein refers to controlling nutrients for the structure and functions of the human body or providing effects useful for health use, such as a psychological effect and the like, and the like. The food of the present invention may be prepared by a method commonly used in the art, and the preparation may be performed by adding raw materials and ingredients commonly added in the art. In addition, the formulation of the food may also be performed without limitation, as long as the formulation is recognized as a food, and the health functional food according to the present invention may be in the form of powders, granules, tablets, capsules, or beverages.

The term "health food" refers to foods having active health maintenance or promotion effect compared to general foods, and "health supplement food" refers to foods for health supplement purposes. In some cases, the terms "health functional food", "health food", and "health supplement food" are used interchangeably.

The food composition may further comprise a physiologically acceptable carrier, and the type of carrier is not particularly limited and may be any carrier that is commonly used in the art.

In addition, the composition may comprise additional ingredients that are commonly used in food compositions to improve smell, taste, eye sight, and the like. For example, the composition may include vitamins A, C, D, E, B1, B2, B6, and B12, niacin, biotin, folate, pantothenic acid, and the like. The composition may also include minerals such as zinc (Zn), iron (Fe), calcium (Ca), chromium (Cr), magnesium (Mg), manganese (Mn), copper (Cu), chromium (Cr), and the like. In addition, the composition may comprise amino acids such as lysine, tryptophan, cysteine, valine, and the like.

In addition, the composition may comprise food additives, such as a preservative (potassium sorbate, sodium benzoate, salicylic acid, sodium dehydroacetate, or the like), a germicide (bleaching powder and high-grade bleaching powder, sodium hypochlorite, or the like), an antioxidant (butylhydroxyanisole (BHA), butylhydroxytoluene (BHT), or the like), a coloring agent (tar color, etc.), a color-fixing agent (sodium nitrite or the like), a bleaching agent (sodium sulfite), a seasoning (MSG or the like), a sweetener (dulcin, cyclamate, saccharin, sodium, or the like), a flavor (vanillin, lactones, or the like), a swelling agent (alum, D-potassium bitartrate, or the like), a reinforcing agent, an emulsifier, a thickener (starch adhesive), a film-forming agent, a gum base agent, an antifoaming agent, a solvent, a conditioner, and the like. The additives may be selected according to the type of food, and may be used in appropriate amounts.

The composition according to the present invention may further comprise, in addition to CSGG polysaccharide or a strain producing the polysaccharide, a sitologically acceptable food supplement additive, may be used in combination with other foods or food ingredients, and may be appropriately used according to a general method. The amount of the active ingredient to be mixed may be appropriately determined according to the purpose of use (prevention, health, or therapeutic treatment).

In another aspect, the present invention is directed to a method of producing induced regulatory T (iTreg) cells comprising the steps of: (a) treating dendritic cells (DCs) with β-1-6-glucan polysaccharide or a *Bifidobacterium bifidum* strain producing the polysaccharide to obtain regulatory dendritic cells (rDCs); and (b) co-culturing the rDCs with $CD4^+$ T cells to induce regulatory T (Treg) cells.

In the present invention, the regulatory T (Treg) cells may be $CD4^+Foxp3^+$ Treg cells. In addition, the regulatory T (Treg) cells may increase the production of IL-10 and TGF-β.

In the present invention, the step (b) may induce regulatory T (Treg) cells by stimulation with an anti-CD3 antibody, IL-2, and TGF-β.

In the present invention, the dendritic cells and the $CD4^+$ T cells may be derived from peripheral blood mononuclear cells (PBMCs), but are not limited thereto.

In another aspect, the present invention is directed to a cellular therapeutic agent for the prevention or treatment of an immune disease or an inflammatory disease comprising induced regulatory T cells (iTregs) produced by the method as an active ingredient.

In another aspect, the present invention is directed to a method of preventing or treating an immune disease or an inflammatory disease, comprising administering a cellular therapeutic agent comprising regulatory T (iTreg) cells produced by the method as an active ingredient.

In another aspect, the present invention is directed to a use of a cellular therapeutic agent for the prevention or treatment of an immune disease or an inflammatory disease, wherein the cellular therapeutic agent comprising induced regulatory T (iTreg) cells produced by the method as an active ingredient.

In the present invention, the regulatory T (Treg) cells may be $CD4^+Foxp3^+$ Treg cells. In addition, the regulatory T (Treg) cells may increase the production of IL-10 and TGF-β.

In the present invention, the immune disease or the inflammatory disease is preferably inflammatory colitis, but is not limited thereto.

*B. bifidum* is one of the dominant bacterial member of intestinal microflora of breastfeeding infants, and deficiency in the bacteria is associated with childhood allergies, asthma, and autoimmune diseases. Some commercial probiotic products include *B. bifidum*, but the efficacy is unclear, and some *Bifidobacterium* species may have harmful effects, such as worsening the progression of rheumatoid arthritis (PNAS, 113(50): E8141-E8150, 2016). Thus, certain components of symbiotic bacteria can be seen to have a beneficial effect on the immune system. The present invention demonstrates that CSGG purified from *B. bifidum* PRI1 is very effective in stimulating Treg cells and can inhibit colitis progression, and thus the immunomodulatory role of bacterial cell wall polysaccharides is considered to be particularly useful for the selection of probiotic bacteria for the treatment of immune and allergic diseases.

By inoculating SPF mice with *B. bifidum* or colonizing GF mice therewith, naive $CD4^+$ cells are allowed to differentiate into peripherally induced Treg (iTreg) cells having the phenotype of $Nrp1^-Foxp3^+$, $Helios^-Foxp3^+$, or $Nrp1^-Helios^-Foxp3^+$ and expressing high levels of IL-10 and CTLA4.

In the present invention, there are proposed two parallel mechanisms by which *B. bifidum* can induce pTreg production in vivo.

First, enhanced levels of butyrate by *B. bifidum* monocolonization may indirectly promote Treg production by directly targeting T cells or by inducing a regulatory DC phenotype (Y. Furusawa et al., *Nature* 504:446-450, 2013; N. Arpaia et al., *Nature* 504:451-455, 2013). That is, the molecular mechanism by which *B. bifidum* stimulates the induction of colon Treg cells may be mediated by at least two types of effector molecules, metabolites (butyrate), and cell surface polysaccharides (CSGG). Previous studies have suggested that butyrate, among short chain fatty acids (SCFAs), a fermentation product produced by symbiotic microorganisms, may be one of the common effector molecules of iTreg inducers. Administration of butyrate-producing bacteria (*Clostridium* butyrate; Atarashi et al., *Nature* 500: 232-236, 2014) or butylated starch to SPF mice led to increased colonic Treg cells by increasing histone H3 acetylation in the enhancer and promoter region of the Foxp3 gene locus (Yukihiro Furusawa et al., *Nature* 504: 446-450, 2013). However, it is not known whether substances derived directly from intestinal microorganisms are able to induce $CD4^+Foxp3^+$ Treg cells.

In one embodiment of the present invention, the cecum size of GF mice was normalized by *B. bifidum* colonization, and the level of butyrate was found to significantly increase in the cecum and feces. In addition to butyrate, cell-surface-derived beta-glucan/galactan polysaccharides (CSGG) were identified as key effector molecules that mimic the Treg-inducing activity of all bacteria. The negatively charged polysaccharide PGβG (phospho glycero-β-galactofuran), which is another polysaccharide isolated from cell surfaces, did not have Treg-inducing activity. PGβG enhanced the Th1/Th17 response. The chemical structure of PGβG is very similar to the lipoteichoic acid (LTA) of pennsylvanicum DSM 20239, a *Bifidobacterium bifidum* subspecies (Fisher W., Eur. J. Biochem. 165 (3): 639-646, 1987). The LTA of gram-positive bacteria generally has pro-inflammatory activity, and when this is eliminated, the anti-inflammatory capacity of probiotic lactic acid bacteria is enhanced (Sara Lebeer, *Trends in Microbiology*, January 2012, Vol. 20, No. 1). These results suggest that the structure of bacterial polysaccharides derived from the same bacterium can differentially regulate the immune response, and it is important to clarify the correlation between the structure and function of polysaccharides derived from symbiotic bacteria.

Second, CSGG derived from the cell surface of *B. bifidum* induces Treg cells through a DC-dependent mechanism (V. K. Raker et al., *Frontiers in immunology* 6:569, 2015). DCs play an important role in CSGG and *Bifidobacterium bifidum*-induced iTreg production. *B. bifidum* and CSGG, an effector molecule thereof, may induce a DC phenotype into regulatory DCs (rDCs) via the TLR/IL-10 pathway. *B. bifidum* colonization or CSGG treatment increases the expression levels of IL-10, TGF-β, GM-CSF, and other Treg-inducing factors in whole colon and cLP-DC ($MHCII^+CD11c^+CD11b^+CD103^+F4/80^-CDF$). Among various Toll receptors (TLRs), TLR2 of DC plays an important role in the detection and transmission of CSGG-induced resistance signals, and TLR2 knock-out DC was shown to be a significant defect in CSGG-induced Treg cell production (about 35% of Treg cell production compared to TLR2 DC). Other studies have also suggested that TLR2 of CD4 T cells (Round J L, 2011 Science) or DCs (Suryasarathi Dasgupta, Cell host and microbes, 2014) plays an important role in the recognition of bacteria-derived polysaccharides for IL-10 production. In addition to TLR2, other receptors may also be involved in CSGG-induced iTreg production because TLR2 KO DC still induces Treg cells. CLR may not be involved because C-type lectin receptor (CLR) inhibitors did not reduce Treg production induced by CSGG. Further research is needed to determine which receptors or combinations thereof are involved in the recognition of CSGG and the transmission of resistance signals for T cells. TGF-β and IL-10 may be key effector molecules of Treg cell differentiation through CSGG-TLR2 signaling in DC. The addition of a TGF-β-blocking antibody completely eliminated CSGG-induced Treg cells. The immunoregulatory cytokine IL-10 plays an important role in the production of CSGG-induced Treg cells. TLR2 KO DCs produced a much lower level of IL-10 and showed reduced activity in inducing Treg cells. These results suggest that IL-10 is a major regulator of immunomodulation in various immune responses (Lochner et al., *The Journal of experimental medicine* 205: 1381-1393, 2008).

In addition, *B. bifidum* colonization or administration of CSGG increases not only RORγt$^+$Foxp3$^+$ Treg cells but also CD103, suggesting that CSGG treatment can induce intestinal Treg cells (B. Yang et al., *Mucosal immunology* 9:444-457, 2016; E. Sefik et al., *Science* 349:993-997, 2015). Colonization of *B. bifidum* may induce dietary- and plant-reactive Treg cells to thus inhibit not only food poisoning but also plant dysregulation. Thus, RORγt$^+$Foxp3$^+$ Treg cells induced by *B. bifidum* or CSGG may be considered to belong to the highly inhibited intestine-specific effector Tregs (M. Esposito et al., *The Journal of Immunology* 185:7467-7473, 2010; D. M. Tartar et al., *The Journal of Immunology* 184: 3377-3385, 2010).

CSGG has very different characteristics compared to capsular polysaccharides A (PSA), the major immunomodulatory molecule of the symbiotic Gram-negative bacterium *Bacteroides fragilis* (Neeraj K. Surana et al., *Immunol Rev.* 245(1):13-26, 2012). Both CSGG and PSA require TLR2/IL-10 signaling to induce Treg cells, but the characteristics of Treg cells are quite different. PSA or outer membrane vesicles (OMV) of *Bacteroides fragilis* predominantly induce IL-10high regulatory T cells but not Foxp3$^+$ Treg cells (Cell Host & Microbe 124: 509-520, 2012; Cell, 122 (1): 107-18, 2005; PNAS. 107(27):12204-9, 2010), and there is no direct evidence for CD4$^+$Foxp3$^+$ Treg cell production. PSA also induces a high level of IFN-γ$^{high}$ Th1 production (Round et al., *Science* 332: 974-977, 2011; Shen et al., *Cell host & microbe* 12: 509-520, 2012). Treg cells induced by PSA have a phenotype such as Foxp3-IL-10$^{high}$IFNγ$^{high}$ (J. L. Round et al., *Science* 332: 974-977, 2011; Y. Shen et al., *Cell host & microbe* 12:509-520, 2012), but most CSGG-induced Treg cells show Foxp3$^+$IL-10$^{high}$IFNγ$^{low}$. PSA promotes IL-12 secretion by activating antigen-presenting cells and induces the activation of dendritic cells rather than inducing resistance (Cell, 122(1):107-18, 2005). CSGG induces Nrp1-Helios-Foxp3$^+$ and RORγt$^+$ Foxp3$^+$ Treg cells producing high levels of IL-10 and CTLA4.

In one embodiment of the present invention, Treg-induced activity was compared between *Bacteroides fragilis* and *B. bifidum* PRI1 in GF mice in vitro and in vivo. Mice monocolonized with *Bacteroides fragilis* showed no increase in Foxp3$^+$ Treg cells and showed IFNγ$^+$IL-10$^{high}$ in CD4$^+$ cells. Cytokine analysis by flow cytometry and ELISA showed high levels of IL-10 and IFN-γ expression in a *B. fragilis*-treated group. In addition, while *B. bifidum* induces Foxp3$^+$ iTreg cells, *B. fragilis* has a high potential to induce IL-10$^{high}$ Tr1 cells rather than Foxp3 Treg cells. In addition, there is no direct evidence that administration of PSA or *Bacteroides fragilis* can enhance CD4$^+$Foxp3$^+$ Treg cells.

Moreover, under suboptimal Treg induction conditions, PSA-treated DCs mainly induced Foxp3IFNγ$^+$IL-10$^{high}$ cells, while CSGG-treated DCs produced Foxp3$^+$IFNγ$^-$IL-10$^{high}$ cells. PSA cannot induce antigen-specific Treg cells because it is processed and presented for T cells bound to MHCII molecules (B. A. CoBb et al., *Cellular microbiology* 7: 1398-1403, 2005). In contrast, CSGG is difficult to load onto MHCII and thus may induce a variety of antigen-specific Treg cells that respond to dietary antigens or symbiotic bacteria. These functional differences may be mediated by differences in chemical structures and mechanisms. PSAs have unique zwitterionic motifs that alternately include positively and negatively charged sugar residues. According to this charge and size, PSA has different activity in T cell stimulation. Native PSAs have an average molecular weight of ~130 kDa, and excessively small fragments (5000 Da fragments) thereof are not active, but 17.1 kDa fragments (~22 repeat units) are reported to have a function of inhibiting colitis (Kalka-Moll W M, et al. *J Immunol.* 164:719-724, 2000). PSA is absorbed into DCs through TLR-2, cut appropriately, and then bound to MHCII molecules to interact with T cells that recognize PSA to thus induce the differentiation of specific helper T cells (CoBb B A et al., *Cell Microbiol.* 7:1398-1403, 2005). In this case, Treg, Tr1 immunoregulatory cells induced by PSA have specificity to PSA, and this phenomenon has a limitation on future antigen-specific Treg cell induction. CSGG is a neutral polysaccharide with an average of ~4000 Da, and unlike PSA, it mainly acts through the regulation of DC properties, rather than directly on T cells. This difference in mechanism of action suggests the possibility of inducing various antigen-specific Treg cells by CSGG treatment. That is, only PSA-specific Treg cells may be generated as the treated PSA is loaded onto MHC II. CSGG, on the other hand, leads to rDCs by inducing phenotypic changes of DCs rather than by endocytosis-mediated processing and loading onto MHC II.

In one embodiment of the present invention, upon administration of CSGG to GF mice, CD4$^+$Nrp$^-$Foxp3$^+$ Tregs cells were significantly enhanced in cLP and MLN. Thus, *B. bifidum* or CSGG treated with all kinds of antigens may induce antigen-specific Treg cells such as dietary-antigen-specific or symbiotic-bacteria-antigen-specific Treg cells. One interesting result is that Bb colonization or administration of CSGG enhances the level of RORγt$^+$Foxp3$^+$ Treg cells in the large intestine. In addition, compared to mock iTreg, iBreg cells induced with Bb or CSGG have a higher population of RORγt$^+$Foxp3$^+$ Treg cells capable of inhibiting enteritis. Compared with the mock-iTreg cells of a colitis model, iTreg cells induced by Bb or CSGG showed sustained Foxp3 expression with higher demethylation status (50% to 60%) in CNS2 of Foxp3 locus. Thus, it is believed that RORγt$^+$Foxp3$^+$ Treg cells induced by Bb or CSGG belong to intestine-specific effector Treg (Esposito et al., *J Immunology* 185: 7467-7473, 2010; Tartar et al., *J Immunology* 184: 3377-3385, 2010; BH Yang et al., *Mucosal Immunology* 9: 444-457, 2016). By studying the role of innate immune cells in this process, the basic mechanism by which Bb or CSGG treatment enhances RORγt$^+$Foxp3$^+$ Treg cells may be further investigated.

The present invention demonstrates that *B. bifidum* PRI1 and effector molecules thereof, CSGG, promote the production of iTreg cells. *Bifidobacterium bifidum* belongs to Actinobacteria, has been specifically identified in human intestines, and has been shown to be one of the important bacterial members of visceral microbiota in breastfeeding infants (Turroni et al., *Applied and environmental microbiology* 75: 1534-1545, 2009). Compared with natural delivery, cesarean delivery resulted in deficiency of *Bifidobacterium* spp., associated with childhood allergies, asthma, and autoimmune diseases. IBD patients have a smaller proportion of *B. bifidum* in feces compared to healthy controls (Wang et al., *Journal of clinical microbiology* 52:398-406, 2014; Verma et al., *Journal of clinical microbiology* 48:4279-428, 2010). Among various types of symbiotic bacteria, *Bifidobacterium* generally has stronger anti-inflammatory properties than *Lactobacillus* in the ability thereof to modulate host responses. However, the immunomodulatory effects of symbiotic bacteria are strain-specific, and identification of functional strains still remains a big challenge. For example, within the same *Bacteroides fragilis*, lipopolysaccharide-producing strains increase inflammatory signals and worsen disease progression (Walter J. Lukiw et al., *Front Microbiol* 7: 1544, 2016). On the other hand, PSA-producing strains are known to inhibit inflammatory diseases. Therefore, it is very important to identify how each of the same species has different immunological properties. As a method for identifying strain-specific immunomodulatory specificity, there is a method of identifying bacteria-derived substances and immunological characteristics thereof and utilizing the substances as functional markers. For example, butyrate may be a marker of Treg-inducing bacteria because butyric acid promotes the differentiation of mesenteric Treg cells (Yukihiro Furusawa et al., *Nature* 504: 446-450, 2013; Liao H Y et al., *Scientific reports*, 6: 20481, 2016). Another method is to identify strains with high genetic homology to known stains by comparative genomic analysis (C. Preston Neff, *Cell Host & Microbe*, 20(4):535-547, 2016). In the present invention, among *B. bifidum* strains, A8 (99.97%) and LMG11582 (99.98%) were found to have the highest base similarity and orthologous genes involved in CSGG synthesis. IPLA 20015 and A8 strains are known as Treg-enhancing bacteria in human PBMC culture systems. As a result of comparing Treg-inducing activity in vitro, the A8 stain showed similar activity to the strain of the present invention, but ATCC 29521 having low base homology (98.9%) and lacking some orthologous genes associated with CSGG synthesis exhibited much lower Treg-inducing activity.

In the present invention, it was confirmed that the administration of *B. bifidum* or CSGG could be used as an oral resistance adjuvant to thus induce various antigen-specific Treg cells in vivo. In addition, *B. bifidum* or CSGG treatment induces rDCs without interfering with antigen presentation in MHC II. Thus, it was confirmed that, when *B. bifidum* or CSGG was administered in combination with autoimmune or allergy-related proteins, antigen-specific Treg cells were induced, thereby inhibiting disease progression. Specific examples of the proteins include autoantigens involved in autoimmune diseases. For example, the proteins may include autoantigens involved in rheumatoid arthritis, such as heat-shock proteins (HSPs), citrullinated filaggrin, glucose-6-phosphate isomerase, p205, collagen, and the like; autoantigens involved in Type I diabetes, such as insulin, Zinc transporter 8 protein (ZnT8), pancreatic and duodenal homeobox 1 (PDX1), chromogranin A (CHGA), and islet amyloid polypeptide (IAPP); and autoantigens involved in myasthenia gravis, such as acetylcholine receptors. In addition to all types of autoantigens known in autoimmune diseases, the proteins may include various allergens known to cause food allergies, such as peanuts, milk, eggs, tree nuts, beans, crustaceans such as shrimp and the like, fish-derived substances, and the like.

The present invention relates to a cell-surface beta-glucan/galactan (CSGG) polysaccharide capable of treating a hyperimmune disease by inducing or producing regulatory T (Treg) cells, and *Bifidobacterium bifidum* PRI1 expressing the same, and the cell-surface beta-glucan/galactan (CSGG) polysaccharide expressed by *Bifidobacterium bifidum* PRI1 is different from polysaccharides of well-known probiotic bacteria, and the CSGG has been found to be an important material inducing the formation of $CD4^+Foxp3^+$Treg cells of probiotic bacteria and exhibits the effect of treating an inflammatory bowel disease or a hyperimmune disease through a mechanism for producing TLR2-mediated DC. In the present invention, the specific structural formula of the cell surface beta-glucan/galactan (CSGG) polysaccharide expressed by *Bifidobacterium bifidum* PRI1 was identified, and it was discovered for the first time that CSGG is a major agonist in inducing regulatory T (Treg) cells. The structure of D-D-glucan of the CSGG of the present invention is beta-1-6-glucan, and the function thereof is completely different from 2-substituted-(1,3)-beta-D-glucan, which is a known D-D-glucan structure. While known D-D-glucan has a prebiotic function, the beta-1-6-glucan of the present invention itself has an immunomodulatory function. In addition, polysaccharides such as polysaccharide A (PSA) do not have the ability to induce antigen-specific Treg other than PSA, whereas CSGG-producing strains are able to induce Treg against materials derived from various kinds of antigens, i.e., foods, other intestinal bacteria, and bacteria themselves, and thus PSA and CSGG completely differ in terms of the structure and mechanism thereof. It is difficult to generalize polysaccharides on the cell surface into a single substance, but the present invention has identified how structural differences are related to function. That is, CSGG itself, which is a substance produced by the bacterium of the present invention, is an active indicator that can represent the function of the bacterium itself that induces Treg.

CSGG may serve as a new functional marker for Treg-inducing bacteria, and CSGG or CSGG-producing *B. bifidum* may be used as a resistance inducing adjuvant to develop specific immunotherapy for autoimmune and allergic diseases.

EXAMPLES

Hereinafter, the present invention will be described in more detail with reference to the following examples. It will be apparent to those of ordinary skill in the art that these examples are provided only to more particularly explain the present invention and are not intended to limit the scope of the present invention according to the gist of the present invention.

Materials and Methods

1. Mouse and Bacterial Strains 1-1: Mouse

Mice were managed at an animal facility at the POSTECH Biotech Center, and all experimental procedures were approved by the POSTECH Institutional Animal Care and Use Committee (IACUC). Germ-free C57BL/6 (B6) mice were received from Drs. Andrew Macpherson (Bern Univ., Switzerland) and David Artis (Then at Univ. Pennsylvania, currently at Cornell University, USA) and established by POSTECH, and maintained by sterile flexible film isolators (Class Biological Clean Ltd., USA). GF status was monitored by cecal contents monthly. Foxp3-eGFP, $Tlr2^{-/-}$, $Tlr4^{-/-}$, $Tlr6^{-/-}$, and $MyD88^{-/-}$ animals were purchased from the Jackson Laboratory. C57BL/6-CD45a(Ly5a)-

Rag1$^{-/-}$TCR OT-II (Rag1$^{-/-}$ OT-II TCR transformants) and Rag1$^{-/-}$ mice were obtained through the Tagonic exchange program. CBir mice were received from O. Elsona (University of Alabama at Birmingham, Birmingham, Ala. 35294, USA; Yingzi Cong, PNAS, 19256-19261, doi: 10.1073/pnas.0812681106). 6-week-old to 12-week-old mice were used in accordance with gender and age.

1-2: Bacteria

B. bifidum PRI1 and other B. bifidum strains were anaerobically cultured in MRS medium (BD, Difco) supplemented with 0.1% L-cysteine, and L. paracasei was cultured in MRS medium. For monocolonization, bacteria ($5\times10^8$ CFU/200 µL) were administered orally to sterile (GF) mice.

2. Purification of Cell Surface Polysaccharides from B. bifidum

The cultured B. bifidum PRI1 was harvested and washed twice with PBS. Purification of cell surface polysaccharides was performed using an existing method that was slightly modified (D. L. Kasper et al., Journal of bacteriology 153: 991-997, 1983). Acidic phenol (Sigma-Aldrich) treatment was performed at 68° C. to extract coating polysaccharides, followed by ether treatment to remove residual phenol and dialysis in distilled water for 3 days. To remove nucleic acids and proteins, treatment with DNase I (Roche) and RNase (Sigma-Aldrich) were performed overnight at 37° C., followed by treatment with Pronase (Protease from Streptomyces griseus, Sigma-Aldrich) at 37° C. overnight. After acetic acid treatment, centrifugation was performed to remove a precipitate. Cooled ethanol was added to precipitate polysaccharides, followed by dialysis in distilled water for 3 days and lyophilization. Purified polysaccharides were dissolved in water and gel filtration was performed using an HPLC column (TSKgel G5000PWXL, Tosho). Anion exchange chromatography (HiPrep Q FF 16/10, GE healthcare) was performed to further separate neutral and negatively charged polysaccharides. The concentrations of polysaccharides were determined by acid phenol analysis (M. DuBois et al., Analytical chemistry 28:350-356, 1956).

3. Bacterial Colonization Analysis by 16S rRNA Gene Analysis

To confirm monocolonization, the genomic DNA of bacteria was isolated from fecal or luminal contents of mice using NucleoSpin DNA Stool (Macherey-Nagel).

PCR analysis was performed using a C1000 touch thermal cycler (Bio Rad), and the primers of Table 1 below were used.

TABLE 1

| SEQ ID NO: | primer | Sequence (5'->3') |
|---|---|---|
| 1 | Total bacteria EUB (forward) | TCCTACGGGAGGCAGCAGT |
| 2 | Total bacteria EUB (reverse) | GGACTACCAGGGTATCTAATCCTGTT |
| 3 | BibiF$^-$ (forward) | CCACATGATCGCATGTGATTG |
| 4 | BibiF$^-$ (reverse) | CCGAAGGCTTGCTCCCAAA |

4. Bacterial Colonization Assay by Fluorescence In Situ Hybridization (FISH)

After 3 weeks of monocolonization by B. bifidum PRI1, mice were sacrificed and the small intestine was divided into 3 segments: the duodenum (within 1 cm to 3 cm at the distal end of the pylorus); the jejunum (within 2 cm to 4 cm from the ligament of Treitz); and the ileum (within 1 cm to 3 cm at the septic valve). 1 cm of each small intestine section and the colon were fixed using Carnoy's solution for histological analysis. The Carnoy's fixing solution (3:1 methanol: glacial acetic acid) was dropped, the cell suspension was centrifuged at 500×g for 5 minutes and then the pellet was re-suspended in Carnoy's fixing solution (Choolani et al., 2007). Paraffin-embedded sections immobilized with Carnoy's solution were dewaxed and hybridized with a Cy5-labeled B. bifidum 16S rRNA fluorescent probe (SEQ ID NO: 5: Bbif, 5'-CCACAATCACATGCGATCATG-3') (Dinoto et al., 2006). The resulting probe was hybridized with hybridization buffer containing 100 ng of a probe (100 nM Tris, pH 7.2, 0.9 M NaCl, 0.1% SDS) in a humidification chamber at 45° C. for 16 hours. Slides were washed in 100 ml of preheated (37° C.) hybridization buffer for 15 minutes, washed with 10 ml of preheated (37° C.) wash solution (100 mM Tris, pH 7.2, 0.9 M NaCl) for 15 minutes (Smith et al., 2011), and then DNA was immunostained with 4',6-diamidino-2-phenylindole (DAPI). The slides were washed with water and air dried, and then images were acquired with a fluorescence microscope (IX70, Olympus, Tokyo, Japan).

5. T Cell Delivery Model of Colitis

Colitis was induced by the adoptive transfer of naive CD4$^+$ T cells in accordance with a previously reported method (A. Izcue et al., Annual review of immunology 27: 313-338, 2009; F. Powrie et al., Immunity 3:171-174, 1995). Naive CD4$^+$CD62L$^{hi}$CD44$^{lo}$Foxp3$^{GFP-}$ T cells (>99% pure, 1×106) sorted along with iTreg cells ($2\times10^5$) induced by B. bifidum PRI1 (Bb), CSGG or mock treatment was intravenously transferred into Rag1$^{-/-}$ mice. The progress of colitis was monitored by weighing twice a week, and the end of the experiment was determined when the mice weighed about 25% of the initial body weight. Using Treg cells as a positive control, ex-vivo-isolated CD4$^+$ Foxp3GFP$^+$ Treg cells ($2\times10^5$) were co-delivered with naive T cells to Rag1$^{-/-}$ mice. The severity of colitis was determined by measuring colon length and histological evaluation at the end of the experiment. Treg cells and cytokine levels were also analyzed.

6. In Vivo Adoptive Transfer

Sorted naive polyclonal CD4$^+$CD62L$^{hi}$CD44$^{lo}$Foxp3$^{GFP-}$ T cells (>99.5% pure) ($1\times10^6$) were intravenously transferred into GF C57BL/6 mice, and a single strain was administered orally. Mice were sacrificed three weeks after the adoptive transfer. To analyze the TCR specificity of Treg cells in response to dietary antigens, naive T cells ($1\times10^6$) isolated from OT-II CD4$^+$CD62L$^{hi}$CD44$^{lo}$Foxp3$^{GFP-}$ T cells were intravenously transferred into GF C57BL/6 mice mono-colonized with B. bifidum PRI1 for 2 weeks before adoptive transfer, and fed with OVA (20 mg/dose/mice) every other day for 7 days. To analyze the TCR specificity of Treg cells in response to symbiotic bacteria, sorted (>99.5% pure) naive CBir CD4$^+$CD62L$^{hi}$CD44$^{lo}$Foxp3$^{GFP-}$ T cells ($1\times10^6$) were delivered intravenously into C57BL/6 mice maintained under SPF conditions, and fed with B. bifidum PRI1 ($5\times10^8$ cfu/dose) three times a week until the experiment was completed. Mice were sacrificed three weeks after adoptive transfer.

7. DC-Dependent In Vitro Induction of iTreg Cells

Colon LP DCs (MHCII$^+$CD11c$^+$CD11b$^+$CD103$^+$F4/80$^-$), spleen total DCs (tDC; MHCII$^+$CD11c$^+$), spleen CD8α$^+$ (MHCII$^+$CD11c$^+$CD11b$^-$), and spleen CD8α$^-$ (MHCII$^+$CD11c$^+$CD11b$^+$) DCs were purified by cell sorting or CD11c magnetic beads (Miltenyi Biotech). The isolated DCs were cultured in complete RPMI 1640 medium containing 10% FBS, 5% penicillin/streptomycin, 2 mM L-glutamine, 1 mM sodium pyruvate, non-essential amino acids, and β-ME. Spleen DCs (2×10⁴) were inoculated into a 96-well plate and cultured for 2 hours, and then cultured with indicated bacteria, a differentiated cell fraction of *B. bifidum* PRI1, or purified polysaccharides of *B. bifidum* PRI1 for 10 hours to 12 hours. Cells were washed and co-cultured with naive CD4⁺ T cells (2×10⁵) for 3 days under suboptimal Treg induction conditions (0.1 μg/ml anti-CD3, 100 U IL-2 and 0.1 ng TGFβ). Levels of cytokines or Treg cells were determined by ELISA and flow cytometry, respectively.

8. Human Samples for DC Differentiation and iTreg Cell Induction by CSGG Treatment The study was approved by the Institutional Review Board (IRB) of Ajou University Hospital (AJIRB-BMR-SMP-17-155), and peripheral blood mononuclear cells (PBMCs) were obtained from healthy donors via Ficoll-Hypaque gradient (Lymphoprep, Nycomed, Norway). Monocytes were isolated from PBMC (CD14+>95%) via positive selection using a CD14 microbead kit (Miltenyi biotech). 5×10⁵ monocytes/ml were cultured in RPMI-1640 medium (2 mM l-glutamine, 25 mM HEPES; BioWhittaker) supplemented with 10% heat-inactivated FCS and antibiotics in a 24-well plate in the presence of rhIL-4 (35 ng/ml) and GM-CSF (70 ng/ml) (R & D Systems, UK) for 7 days. On days 2 and 5, 0.5 ml of medium was replaced with fresh medium containing GM-CSF and IL-4. On day 7, immature DCs were recovered and pretreated with mock or different amounts of CSGG for 14 hours. Next, the cells were cultured with naive CD4⁺ T cells isolated from human PBMC for 3 days under suboptimal Treg induction conditions (0.1 μg/ml anti-CD3, 100 U IL-2 and 0.1 ng TGFβ). Levels of Treg cells were determined by flow cytometry.

9. Data Availability for RNA-Seq

Total RNA was extracted from spleen CD11c⁺ DCs stimulated for 4 hours with mock or CSGG (100 μg/ml) and purified by Ribospin™ II (GeneAll biotechnology). RNA quantification and quality control were performed using a NanoDrop 2000™ (Thermo Fisher Scientific). Library preparation was performed with a TruSeq Stranded mRNA Sample Preparation Kit (Illumina), and RNA sequencing was performed using a NextSeq 500 Sequencing System. RNA-seq data was deposited in the Gene Expression Omnibus (NCBI) data store under the accession number GEO: RNA-seq data: GSE98947.

10. RNA Isolation and Real-Time Quantitative RT-PCR

Total RNA isolated from colon and cLP DCs using TRIzol reagent (Invitrogen) was reverse transcribed using M-MLV reverse transcriptase (Promega, Madison, Wis., USA) to prepare cDNA. The synthesized cDNA was subjected to quantitative real-time PCR (qRT-PCR) using the following primer sets (Table 2) and a CHROMO4 Detector (Biorad).

TABLE 2

| SEQ ID NO: | primer | Sequence (5'->3') |
|---|---|---|
| 6 | HPRT (forward) | TTA TGG ACA GGA CTG AAA GAC |
| 7 | HPRT (reverse) | GCT TTA ATG TAA TCC AGC AGG T |
| 8 | IL-10 (forward) | ATA ACT GCA CCC ACT TCC CA |
| 9 | IL-10 (reverse) | TCA TTT CCG ATA AGG CTT GG |

TABLE 2-continued

| SEQ ID NO: | primer | Sequence (5'->3') |
|---|---|---|
| 10 | TGF-β (forward) | CTC CCG TGG CTT CTA GTG C |
| 11 | TGF-β (reverse) | GCC TTA GTT TGG ACA GGA TCT G |
| 12 | IL-β (forward) | CAA CCA ACA AGT GAT ATT CTC C |
| 13 | IL-β (reverse) | TGC CGT CTT TCA TTA CAC AG |
| 14 | Csf2 (forward) | AGG GTC TAC GGG GCA ATT TC |
| 15 | Csf2 (reverse) | GGC AGT ATG TCT GGT AGT AGC TG |
| 16 | PD-L1 (forward) | GCT CCA AAG GAC TTG TAC GTG |
| 17 | PD-L1 (reverse) | TGA TCT GAA GGG CAG CAT TTC |
| 18 | IDO (forward) | GCT TTG CTC TAC CAC ATC CAC |
| 19 | IDO (reverse) | CAG GCG CTG TAA CCT GTG T |
| 20 | COX2 (forward) | TGG CTG CAG AAT TGA AAG CCC T |
| 21 | COX2 (reverse) | AAA GGT GCT CGG CTT CCA GTA T |
| 22 | CD80 (forward) | ACC CCC AAC ATA ACT GAG TCT |
| 23 | CD80 (reverse) | TTC CAA CCA AGA GAA GCG AGG |
| 24 | CD86 (forward) | TGT TTC CGT GGA GAC GCA AG |
| 25 | CD86 (reverse) | CAG CTC ACT CAG GCT TAT GTT TT |
| 26 | CD40 (forward) | CCT TGC ACT GTG AGG AGA |
| 27 | CD40 (reverse) | CTT CGC TTA CAA CGT GTG CT |

All qRT-PCR procedures were performed under the same conditions at 40 cycles for 5 minutes at 95° C., 30 seconds at 95° C., 30 seconds at 62° C., and 30 seconds at 72° C. Data was normalized to values of HPRT expression levels. The results were described as relative expression levels for each gene between treatment groups.

11. Lymphocyte Isolation and Flow Cytometry

Naive CD4⁺ T cells were purified from mLN, pLN, and spleen using a cell separator (purity of 98% or more). The large intestine and small intestine of mice were opened in the longitudinal direction and mucus was removed by washing with PBS. The large intestine was cut into small pieces and shake-cultured for 20 minutes at 37° C. with 10 mM EDTA, 20 mM Hepes, 1 mM sodium pyruvate, 3% FBS and PBS without Ca²⁺ and Mg²⁺. The tissue was ground into smaller pieces with a razor and shake-cultured in RPMI 1640 medium containing 3% FBS, 20 mM Hepes, 1 mM sodium pyruvate, and 0.5 mg/ml of Collagenase D (Roche) and DNaseI (Sigma) at 37° C. for 45 minutes. After enzymatic treatment, the supernatants were filtered with cold PBS containing 10 mM EDTA using a 100 µm cell filter. Cells were placed on a Percoll™ (GE Healthcare) gradient (top 40% Percoll, bottom 75% Percoll) and centrifuged without interruption at 2000 rpm for 20 minutes. Cells in the layer between 40% and 75% were taken and washed twice with RPMI medium (Hyclone SH30027.01) containing 10% FBS (Hyclone), Pen/Strep, β-ME, sodium pyruvate, and 2.0 mM L-glutamine and used for FACS staining. Cell suspensions were first stained Live/dead in PBS using LIVE/DEAD fixable viable dye (eBioscience) or PI. Thereafter, further staining was performed in a buffer containing 1% FBS (Gibco) and EDTA (Sigma-Aldrich). Surface staining was performed in PBS containing 0.2% bovine serum albumin for 20 minutes. For intracellular transcription factor staining, cells were stained with fixation/permeabilization buffer (eBioscience) and 1× permeabilization/wash buffer (eBioscience). For intracellular cytokine analysis, purified lamina propria lymphocytes were restimulated with 500 ng/ml of Ionomycin (Calbiochem) and 100 ng/ml of PMA (Calbiochem) using GolgiPlug (BD biosciences, 0.5 µL/sample) at 37° C. for 4 to 5 hours. The cells were fixed in an IC fixation buffer (eBioscience), and permeability was imparted thereto in a permeabilization/wash buffer (eBioscience), followed by staining with IL-10, IL-13, IFN-γ and IL-17A antibodies.

The following antibody clones were used. CD4 (RM4-5), CD44 (IM7), CD62L (MEL-14), CD45.1 (A20), CD45.2 (104), CD90.1 (Thy1.1) (OX-7), CD90.2 (Thy1.2) (30-H12), CD103 (2E7), Va2 (B20.1), Foxp3 (FJK-16s), CTLA4 (UC10-4B9), Nrp1 (3E12), Helios (22F6), T-bet (4B10), RORγt (AFKJS-9), GATA-3 (16E10A23), IL-10 (JES5-16E3), IL-13 (eBio13A), IFN-γ (XMG1.2), IL-17A (17B7), CD11c (N418), CD11b (M1/70), F4/80 (BM8), MHCII (M5/114.15.2).

For flow cytometric sorting, dead cells were excluded and populations were gated with followings: LP DCs (CD45$^+$ MHCII$^+$CD11c$^+$CD11b$^+$ CD103$^+$F4/80$^-$), SP DCs (MHCII$^+$CD11c$^+$CD11b$^+$CD8α$^+$ or MHCII$^+$CD11c$^+$CD11b$^+$ CD8α$^+$), naive CD4$^+$ T cells (CD4$^+$CD45.1$^+$CD62L$^{hi}$CD44$^{lo}$Foxp3$^{GFP-}$), naive OT-II TCR transgenic T cells (CD4$^+$CD90.1$^+$OT-II$^+$CD62L$^{hi}$CD44$^{lo}$Foxp3$^{GFP-}$ CBir TCR transgenic naive T cells (CD4$^+$CD45.1$^+$CD62L$^{hi}$CD44$^{lo}$Foxp3$^{GFP-}$) Cell sorting performed using Moflo-XDP and flow cytometry was performed using an LSR Fortessa flow cytometer (BD Biosciences) equipped with five lasers. Data was analyzed using FACSDiva software (BD Biosciences) and FlowJo software.

12. TCR Repertoire Analysis Using CDR3 High-Throughput Sequencing

Total RNA was extracted from sorted CD4$^+$Foxp3$^{GFP+}$ Treg cells of GF mice or mice mono-colonized with *B. bifidum* PRI1 for 3 weeks. Dead cells were excluded by FVD staining using an ISOGEN kit (Nippon Gene). Next-generation sequencing was performed using an unbiased TCR repertoire analysis technique of Repertoire Genesis Inc. Adaptor-ligation PCR was performed by an existing method (R. Yoshida et al., Immunogenetics 52: 35-45, 2000). The first double-stranded cDNA was synthesized with Superscript III reverse transcriptase (Invitrogen), ligated with a 5' adapter oligonucleotide, and then PCR amplified using primers specific to the adapter and TCRα constant region or TCRβ constant region. After amplification of TCRα and TCRβ cDNA, index (barcode) sequences were added using a Nextera XT Index Kit v2 setA (Illumina). Sequencing was performed using an Illumina Miseq paired-end platform (2×300 bp). Data processing was performed using Repertoire Analysis software from Repertoire Genesis, Inc. TCR sequences were assigned using a possible data set of reference sequences from the International ImMunoGeneTics Information System (IMGT) Database (http://www.imgt.org). After removing low-scoring sequences, TCR repertoire analysis was performed using bioinformatics software developed by Repertoire Genesis Incorporation (Ibaraki, Japan). Sequence reads that are not identical to other sequence reads are defined as unique sequence reads (USRs). Copy numbers of the same USR are automatically calculated by the RG software.

13. Effect of TGF-β Neutralization on iTreg Cell Production In Vitro

Spleen MHCII$^+$CD11c$^+$ DCs (2×10$^4$) were inoculated into a round-bottom 96-well plate for 2 hours, and then cultured with *B. bifidum* PRI1 or CSGG for 12 hours. The cells were washed and co-cultured with naive CD4$^+$ T cells (2×10$^5$) in the presence of 0.1 µg/ml of anti-CD3 (BD Bioscience), 100 U IL-2 (Peprotech), and 0.1 ng/ml of TGF-β or in the absence of 15 µg/ml of anti-TGF-β antibody (R & D). After culture for 3 days, the population of CD4$^+$Foxp3$^+$ T cells was analyzed using flow cytometry.

14. In Vitro Inhibition Assay

In vitro-generated CD45.1$^+$CD4$^+$Foxp3$^{GFP}$ iTreg cells were sorted and cultured with pulse treated-reactive cells (Thy1.1$^+$CD4$^+$Foxp3$^-$) at 37° C. for 10 minutes. Cells labeled with CTV were washed twice with PBS and used immediately. T cells removed-splenocytes (1×10$^5$), CTV-pulsed reactive cells (5×10$^4$), and indicated amounts of iTreg cells were mixed with 0.5 µg/ml of anti-CD3 in a round-bottom 96-well plate. The cells were cultured for 4 days, and proliferation thereof was analyzed by flow cytometry to determine dilution of CTV intensity. The suppression rate (%) was calculated as the total percentage of dividing cells by comparing the percentage of responder's cells alone.

15. Histology

Clinical conditions of experimental colitis were evaluated by histological analysis with H & E staining. Colons were collected and fixed in 10% formaldehyde. After fixation, tissues were embedded into paraffin blocks and cut to 3 µm thickness and stained with hematoxylin (Sigma-Aldrich) and eosin (Sigma-Aldrich).

16. Statistical Analysis

Statistical analysis was performed with GraphPad Prism software (La Jolla, Calif.), and the differences between control and experimental groups were evaluated using unpaired-Student's t-test. Data was expressed as mean±SEM. For in vivo stability analysis of Treg cells and experimental colitis, statistical analysis was performed using two-way analysis of variance with Bonferroni's multiple comparison test. P<0.05 was considered significant.

Example 1: Treq-Inducing Bacteria Screening

Enhancing Treg cells in vivo by immunoregulatory microorganisms enables the regulation of dysbiosis associated with inflammatory disorders. To identify Treg-inducing bacteria among microorganisms which are regarded as safe, 200 or more strains of probiotics were screened using the previously reported ex vivo screening system (Kwon et al, *PNAS* 107:2159-2164, 2010, Kim J E, *J Funct Foods*. 350-362, 2015).

Each bacterial strain was co-cultured with mesenteric lymph node (mLN) cells of Foxp3 reporter mice in the presence of antibiotics (Gentamycin®). The levels of Foxp3, IL-10, and IL-12 were measured to select strains in which an IL-10/IL-12 ratio was >100 and increasing Foxp3 expression by at least 10%.

As a result, *Bifidobacterium bifidum* PRI1 (*B. bifidum*; Bb) was selected as an optimal candidate for Foxp3$^+$ Treg-inducing bacteria (see FIGS. 2A and 2B), and *Lactobacillus paracasei* sub. *tolerans* 467 (*L. paracasei*; Lpa) was selected as a control strain that did not induce an immune response. The selected *Bifidobacterium bifidum* PRI1 was deposited on May 19, 2017 at the Korean Collection for Type Cultures of the Korea Research Institute of Bioscience and Biotechnology (Accession Number: KCTC13270BP).

Example 2: Treq Cell Induction by *B. bifidum*

It was examined whether *B. bifidum* is able to induce Treg cells in vivo.

Segmented filamentous bacteria (SFB) were used as Th17-inducing control bacteria. Through single administration of *B. bifidum* (Bb) to germ free (GF) mice, the bacterium was stably colonized in the colon (see FIG. 2C), and the enlarged cecum size was normalized to a size similar to that of normal SPF mice (see FIG. 2D). This means the fibrous digestive activity of Bb. In addition, short chain fatty acids (SCFAs), such as butyrate and acetate, are end products of dietary fiber fermentation, so mice colonized with Bb exhibited no change in propionate level and a significant increase in levels of acetate and butyrate in cucum and feces (see FIG. 2E).

Figure 2:
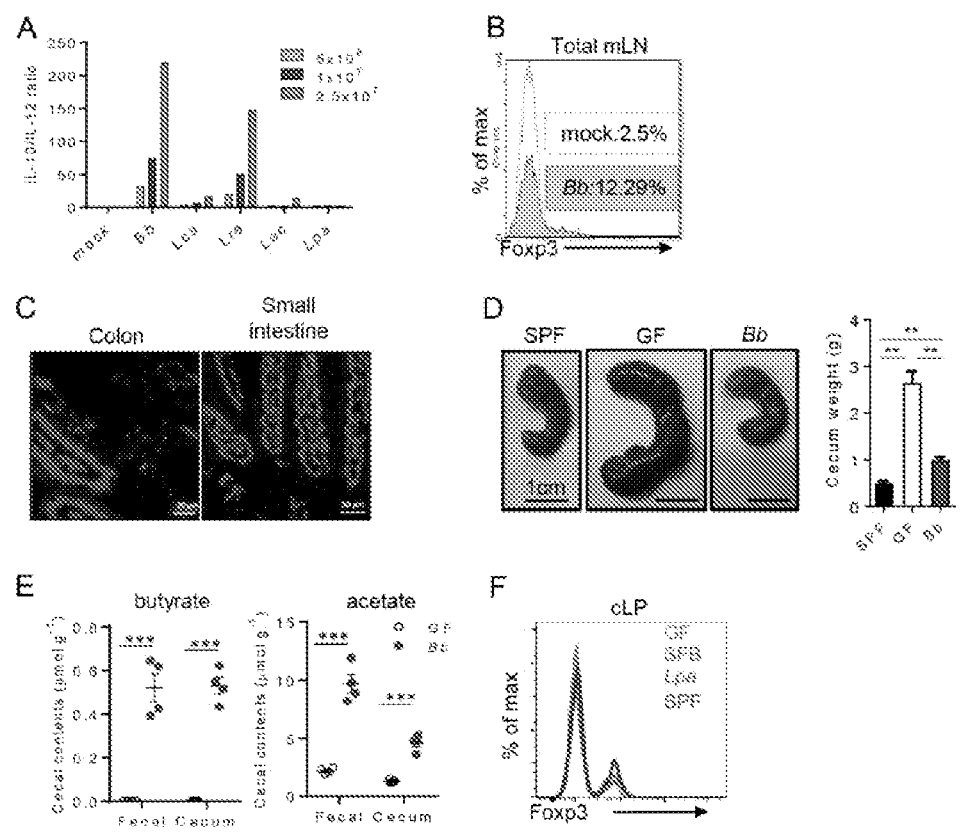
FIG. 2 illustrates the results of confirming *B. bifidum* PRI1 as Treg-inducing bacteria.
Figure 3:
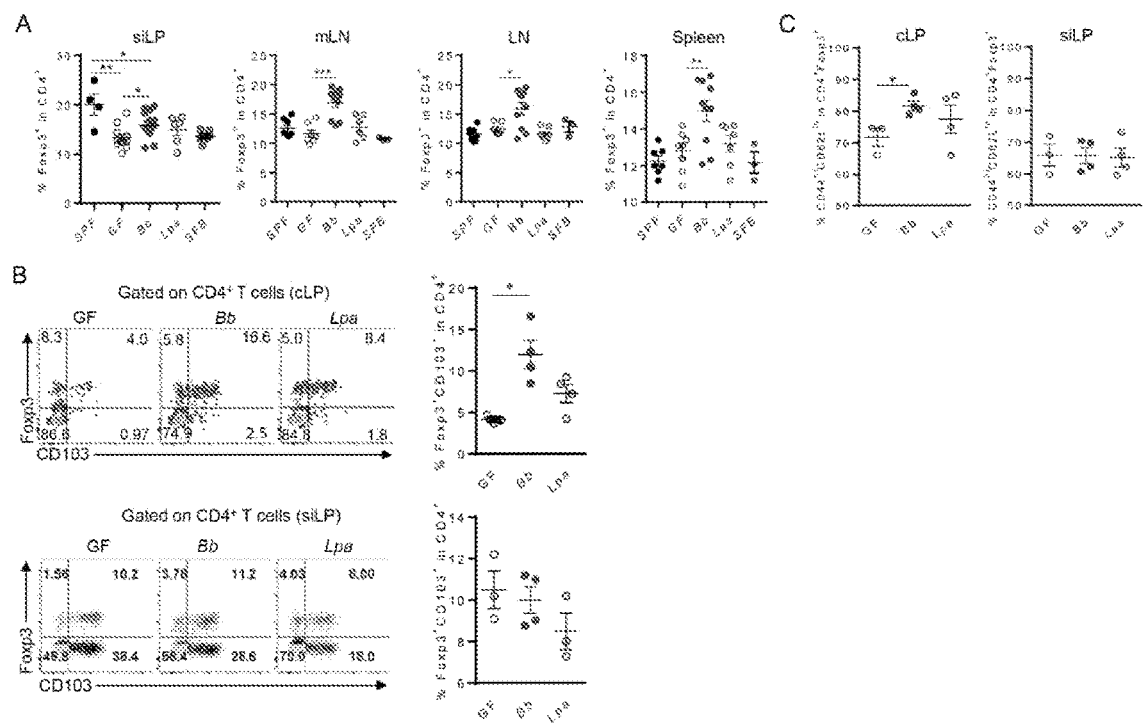
FIG. 3 illustrates the effect of *B. bifidum* monocolonization on the production and phenotype of Treg cells.
Figure 4:
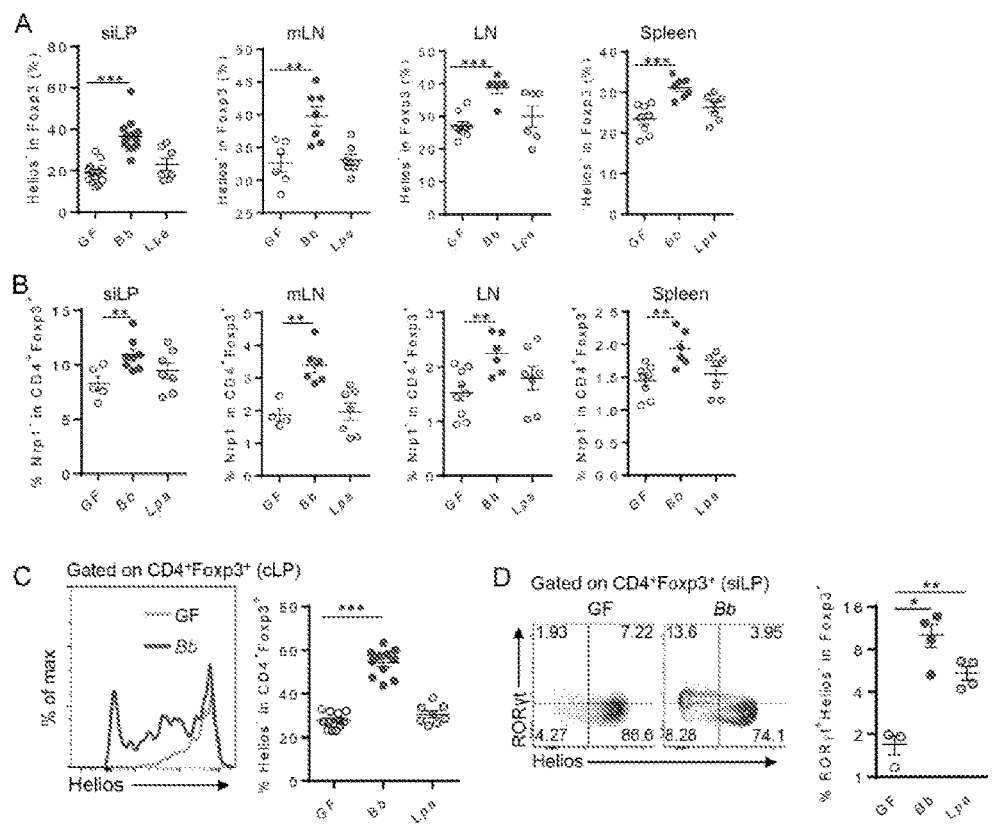
FIG. 4 illustrates an increase of the Treg population in other lymphoid organs, caused by *B. bifidum* monocolonization, wherein cells were isolated from the lymphoid organs of GF mice or mice at 3 weeks after monocolonization with Bb or Lpa.

Unlike *L. paracasei* (Lpa) or SPF, GF mice colonized with *B. bifidum* (Bb) for 3 weeks exhibited a drastic increase in the frequency of Foxp3$^+$ Treg cells in the colon lamina propria (cLP) (see FIGS. 1A and 2F). In addition, Treg cells were slightly increased in other organs such as mesenteric lymph nodes (MLN), spleen, small intestine lamina propria (siLP), and peripheral lymph nodes (LN) (see FIG. 3A). Treg cells in the colon lamina propria (cLP) of GF mice colonized with *B. bifidum* (Bb) exhibited significantly higher proportions of CD103$^+$ and memory phenotype (CD62L$^{lo}$CD44$^{hi}$) (see FIGS. 3B and 3C) and also exhibited high levels of CTLA4 and IL-10 (see FIGS. 1B and 1C).

Example 3: Newly Produced iTreq by Bb

Since Treg cells can be further differentiated into thymus-derived Treg (tTreg) or peripherally induced Treg (pTreg or iTreg), the origin of Treg was tracked by analyzing Helios and Nrp1 expression in Treg cells.

To distinguish Helios$^+$ Nrp1$^+$ thymus-derived Treg (tTreg) from Helios$^-$ Nrp1$^-$ periphery-derived Treg (pTreg) (referred to as "iTreg" in the case of production under in vitro culture conditions), the expression of IKAROS family transcription factors Helios and Neuropilin 1 (Nrp1) was observed (J. M. Weiss et al., *The Journal of experimental medicine* 209:1723-1742, 2012; E. M. Shevach et al., *Immunological reviews* 259:88-102, 2014; J. P. Edwards et al., *The Journal of Immunology* 193: 2843-2849, 2014).

As a result, Nrp1$^+$ tTreg cells slightly increased in cLP colonized with *B. bifidum*, but Nrp1$^-$ and Helios$^{lo}$ pTreg cells increased much more in all organs (see FIGS. 1D to 1F and FIGS. 4A to 4C). In addition, a large fraction of newly produced pTreg expressed the transcription factor RORgt (see FIGS. 1G and 4D), and this is upregulated by interaction with microorganisms (B. Yang et al., *Mucosal immunology* 9:444-457, 2016; E. Sefik et al., *Science* 349:993-997, 2015).

Figure 5:
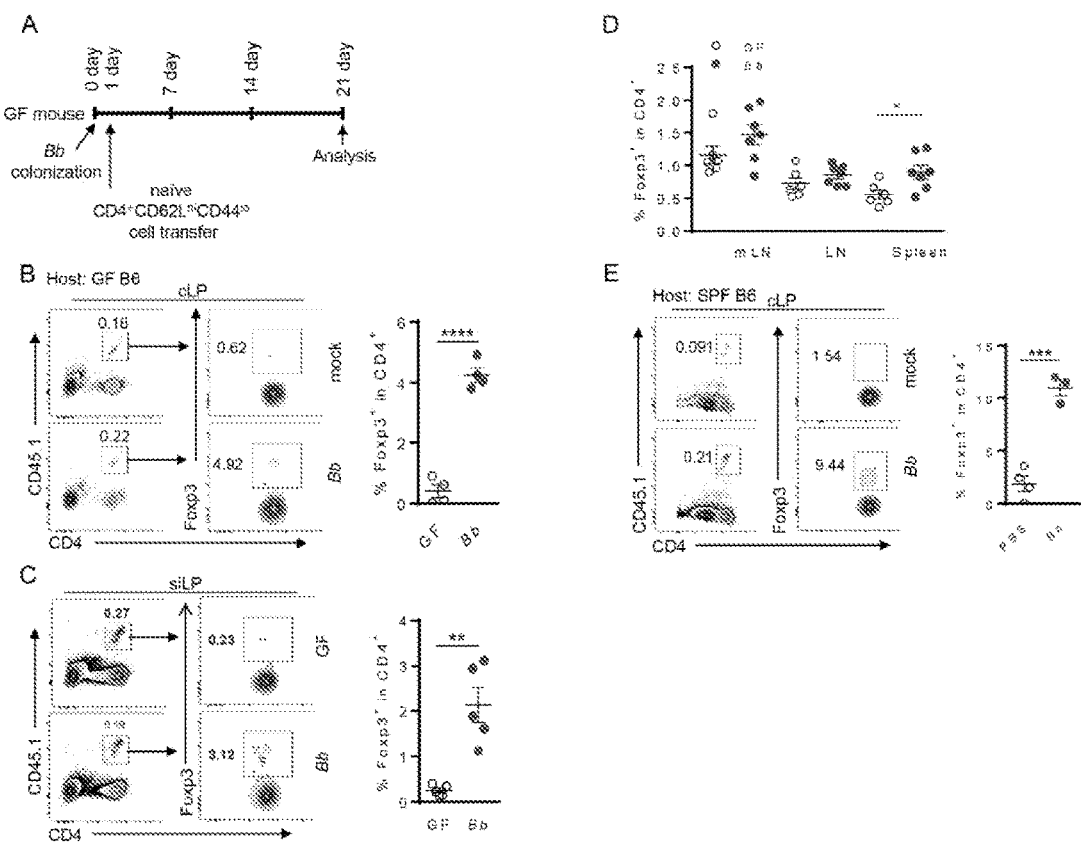
FIG. 5 shows that *B. bifidum* monocolonization promotes new growth of pTreg cells.

Next, to confirm that the increase in Treg cells induced by Bb colonization is not expansion of existing Treg cells, but new production from naive CD4$^+$ T cells of peripheral tissues, an adoptive transfer experiment was performed. The peripheral origin of *B. bifidum*-induced Treg cells was determined by adoptive transfer of allelically-marked naive CD4$^+$CD45.1$^+$Foxp3$^-$CD62L$^{hi}$CD44$^{lo}$ T cells sorted from Foxp3$^{GFP}$ to GF mice mono-colonized with *B. bifidum* (see FIG. 5A).

As a result of donor cell analysis after 3 weeks, a large fraction of Foxp3$^+$ Treg cells among donor cells was shown in the intestine of GF mice colonized with *B. bifidum* (cLP) (see FIGS. 4A to 4D). The induction of pTreg cells was similarly increased in SPF mice to which *B. bifidum* was administered for 3 weeks (see FIG. 5E). These results indicate that the administration of *B. bifidum* enables new production of iTregs manly from naive CD4 T cells in the colon.

Example 4: Analysis of TCR Specificity of pTreg Cells

The TCR specificity of pTreg cells produced in the presence of *B. bifidum* was analyzed. It was tested whether *B. bifidum* colonization promotes pTreg cells in dietary antigens, i.e., whether *B. bifidum* colonization can increase the production of dietary antigen-reactive iTreg cells. CTV-labeled naive CD4$^+$ Thy1.1$^+$Foxp3$^-$ T cells of OVA-specific TCR-transformed OT-II mice were adoptively transferred into GF mice, and then the mice were colonized with Bb or left without colonization, followed by supply of an oral OVA protein. That is, CTV-labeled OVA-specific naive CD4$^+$ cells of OT-II.Thy1.1$^+$Foxp3$^{GFP}$ mice were adoptively transferred into normal or *B. bifidum*-colonized GF mice to which the OVA protein was administered (see FIG. 7A).

As a result, as previously observed (K. S. Kim et al., *Science* 351: 858-863, 2016), a small fraction of expanded OT-II cells in normal GF hosts upregulated Foxp3 in siLP and cLP (see FIGS. 6A and 6B). That is, compared with the GF OVA-fed mice, the mice colonized with Bb exhibited a significant increase in Thy1.1$^+$OT-II-specific Foxp3$^+$ Treg cells and host-derived Treg cells, mainly in cLP. In particular, the efficiency of upregulation of Foxp3 by donor OT-II cells in mice colonized with *B. bifidum* increased 2-fold to 3-fold in cLP, but did not change in siLP and mLN (see FIG. 6B).

Example 5: Production of Microbiota-Specific pTreg Cells

To determine whether *B. bifidum* colonization promotes the production of microbiota-specific pTreg cells, CBir TCR transgenic mice recognizing bacterial flagellin were used (Y. Cong et al., *The Journal of Immunology* 165: 2173-2182, 2000). Naive CD4$^+$Foxp3$^-$ T cells were sorted from CBir transgenic mice on a CD45.1$^+$Foxp3$^{GFP}$ background and adoptively transferred into SPF Rag1$^{-/-}$ recipients, followed by supply of mock (PBS) or *B. bifidum* every other day for 5 weeks (see FIG. 7B).

As a result, control SPF Rag1$^{-/-}$ recipients of CBir T cells alone showed prominent signs of colitis as indicated by progressive weight loss (see FIG. 6C), few Treg cells (see FIG. 6F), a high proportion of CD4$^+$IFNγ and RORγ$^+$ Foxp3$^-$ T cells (see FIGS. 6G and 7C), a shortened colon (see FIG. 6D) with thickened mucosa (see FIG. 6E), and the like. These various signs of pathology were nearly absent in hosts injected with CBir T cells in combination with *B. bifidum* administration (see FIGS. 6C to 6G and 7C).

Example 6: Specificity of iTreq Cells for *B. bifidum* Itself

Figure 7:
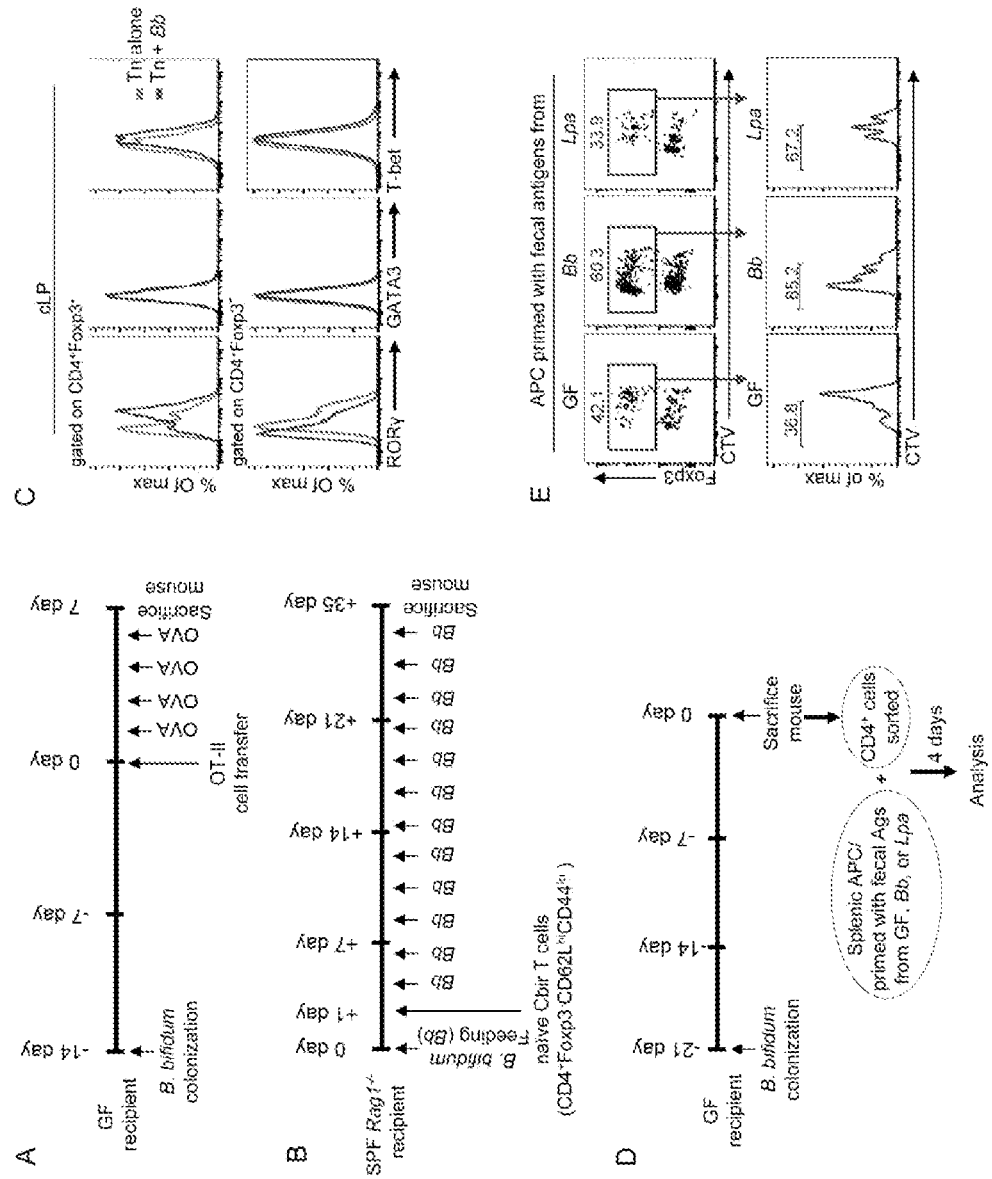
FIG. 7 illustrates dietary antigen and microbiota-reactive Treg cell induction by *B. bifidum* colonization.
Figure 8:
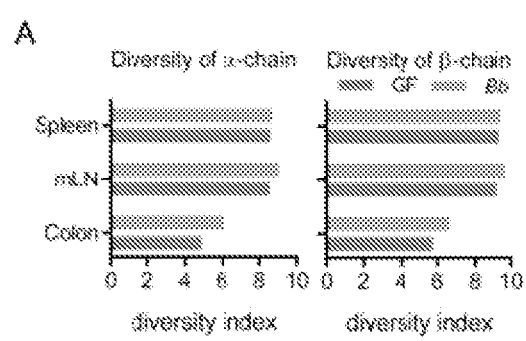
FIG. 8 illustrates the effect of *B. bifidum* monocolonization on TCR repertoire of Treg cells.
Figure 8:
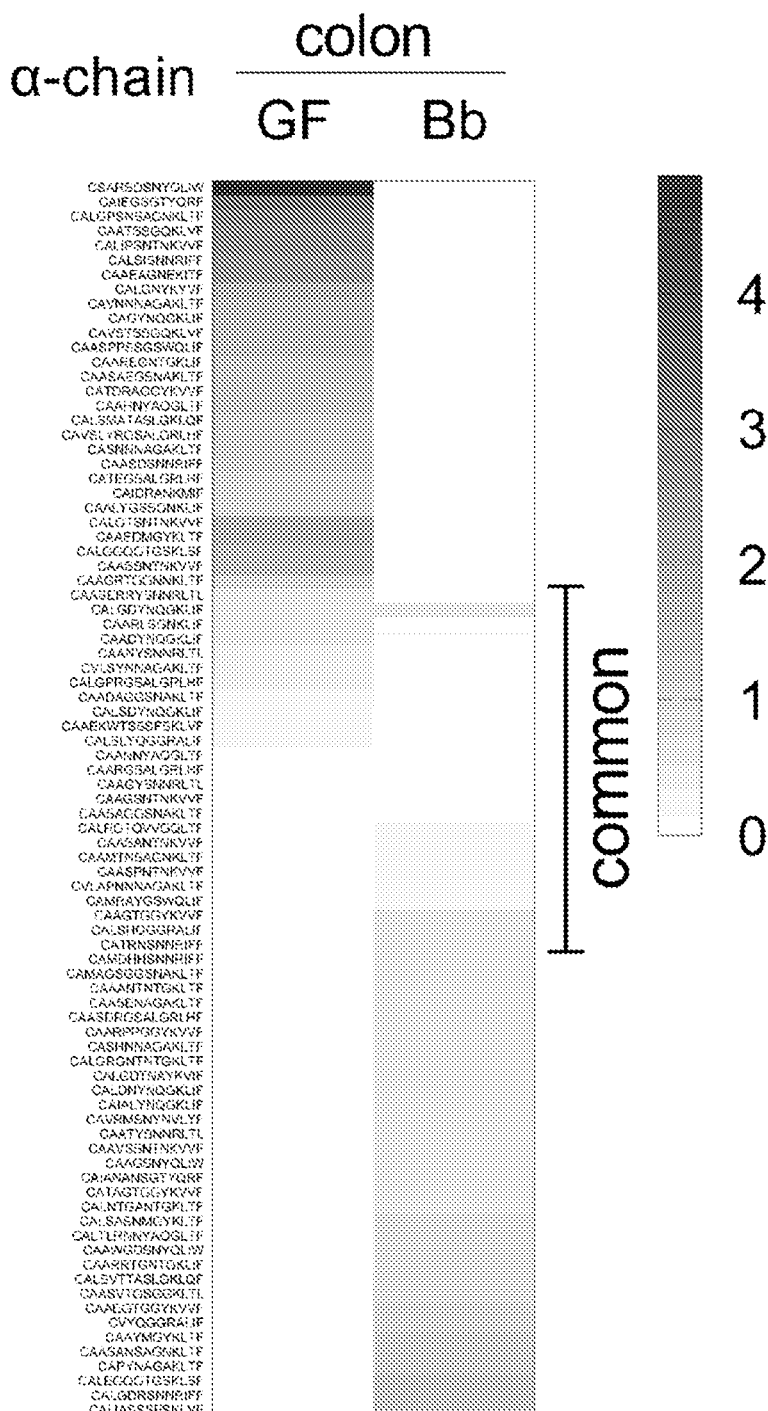
Figure 8:
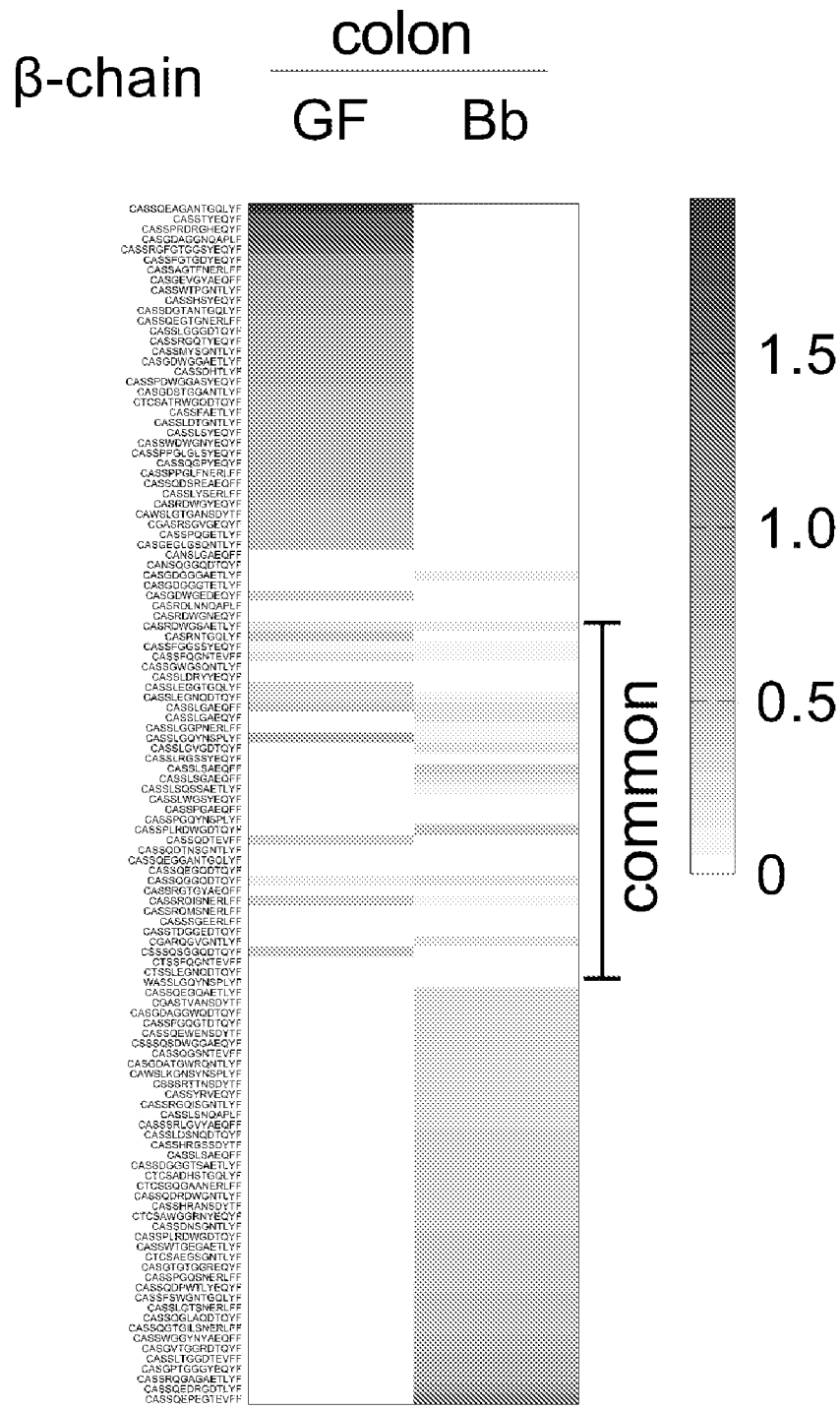
Figure 8:
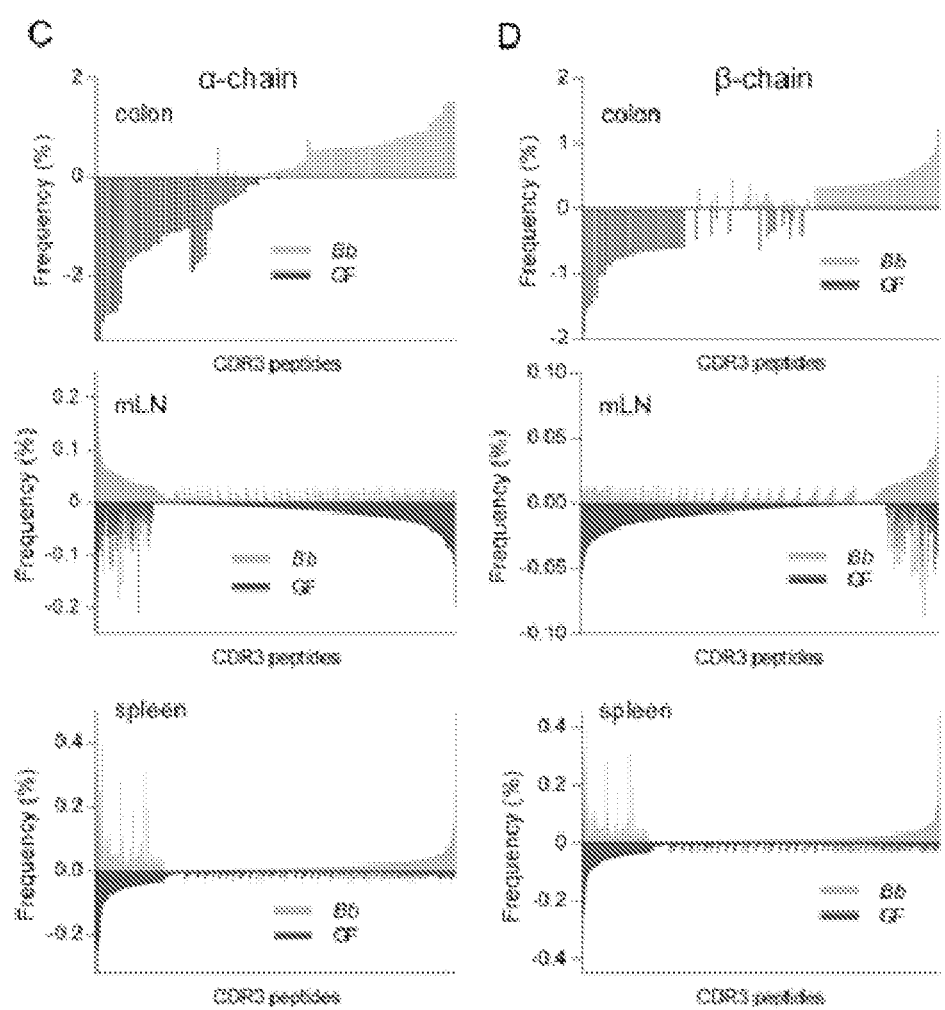

To test whether the pTreg cells induced by *B. bifidum* have specificity for *B. bifidum* itself, total colonic CD4+ T cells of GF mice colonized with *B. bifidum* were co-cultured with splenic APCs pretreated with fecal antigens from normal GF mice and GF mice colonized with *B. bifidum* or *L. paracasei*, and after 3 days, T cell proliferation (CTV dilution) of these cells was analyzed (see FIG. 7D).

Figure 6:
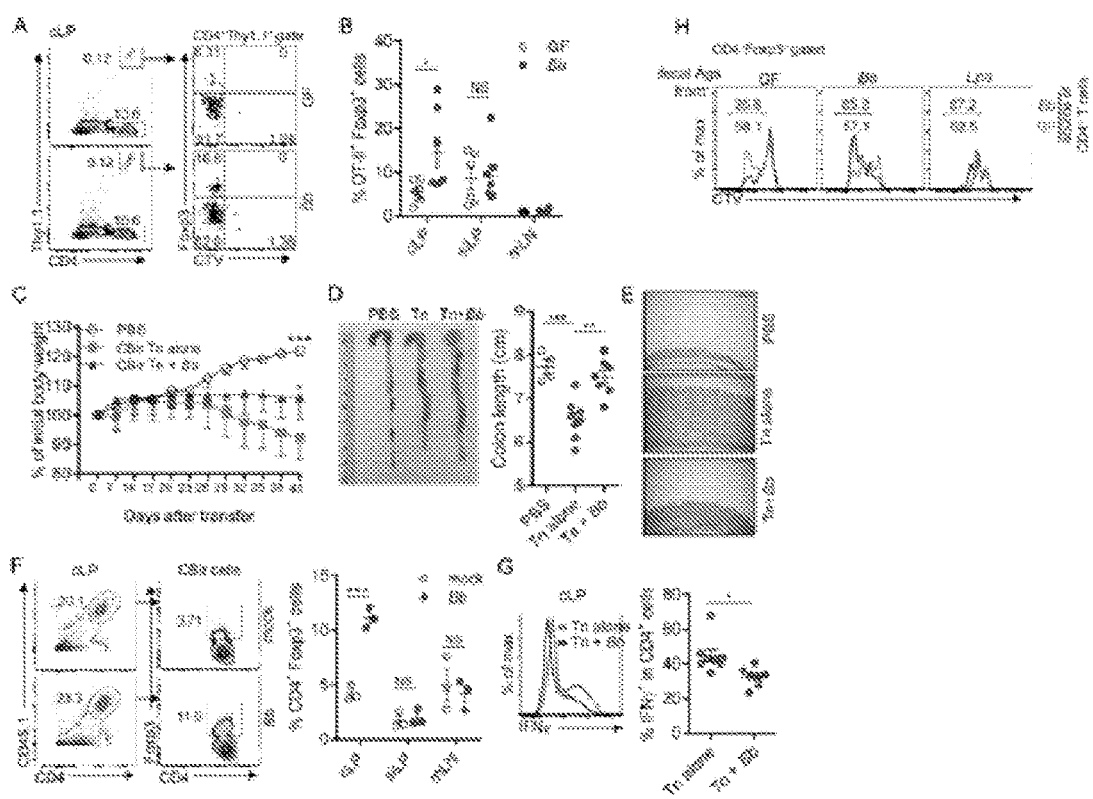
FIG. 6 illustrates dietary antigen and microbiota-reactive Treg cell induction by colonization with *B. bifidum*.
Figure 6:
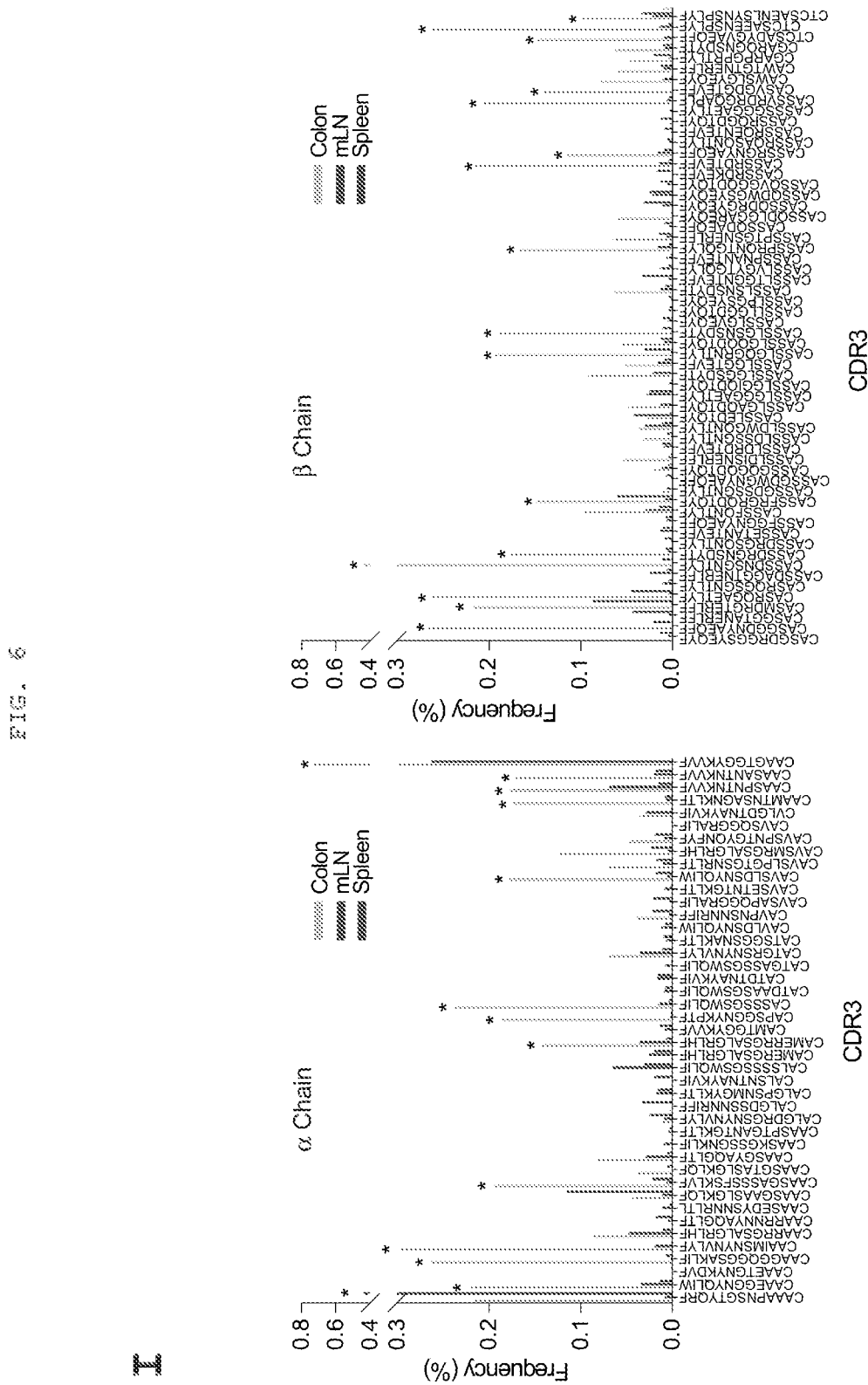

As a result, most Treg cells died under in vitro culture conditions, whereas Foxp3+ Treg cells of GF mice colonized with *B. bifidum* sustained Foxp3 expression and proliferation when stimulated with *B. bifidum* Ag-treated APCs (see FIGS. 6H and 7E).

In addition, TCR specificity of GF and *B. bifidum*-monocolonized mice was compared by sequencing the α- and β-chains of Foxp3+ Treg cells sorted from colon, mLN, and spleen.

As a result, although both Treg cells showed a similar pattern of diversity in α- and β-chains (see FIG. 8A), colonic Treg cells from *B. bifidum*-colonized mice showed separate TCR patterns that were not present in GF control (see FIGS. 6I and 8A to 8D). Collectively, these results suggest that *B. bifidum* induces functionally active CD4+Foxp3+ Treg cells with a broad range of TCR specificity to dietary antigens and/or commensal microbiota and *B. bifidum* itself.

Example 7: rDCs Induction and New pTreg Differentiation Enhancement by *B. bifidum* Colonization It was examined whether colonization by *B. bifidum* induces a population of regulatory dendritic cells (rDCs), which may enhance new pTreg differentiation.

Since differentiation of naive T cells into iTreg cells requires an immunoregulatory cytokine environment, it was tested whether colonization of *B. bifidum* induces a tolerogenic environment in the colon. Compared with GF mice, cLP-DCs (MHCII+CD11c+CD11b+CD103+F4/80−) isolated from Bb-colonized mice and total colonic cells significantly increased not only mRNA expression of inhibitory molecules such as Il10, Csf2, Tgfβ1, ido, Ptgs2, Pdcd1, but Cd86 and Cd40, which are costimulatory molecules (see FIGS. 10A to 10D). This suggests that colonization of Bb can induce regulatory dendritic cells (rDCs) that promote the differentiation of iTreg cells.

In addition, an in vivo mimicking experiment was performed by culturing sorted cLP-DC with *B. bifidum* for 10 to 12 hours followed by washing and then co-culture with naive CD4+Foxp3− T cells for 3 days under suboptimal Treg-inducing conditions. As a result of pretreatment of cLP-DC with *B. bifidum*, induction of the production of iTreg cells and IL-10 and proliferation thereof were increased compared with a mock-treated group or a control treated with *L. paracasei* (Lpa) (see FIGS. 10E to 10G).

Example 8: Identification of Effector Molecules of *B. bifidum*

8-1: Effector Molecules of *B. bifidum*

Using an in vitro system, broad experiments were performed to identify *B. bifidum*-derived effector molecules that promote iTreg differentiation. Since *B. bifidum* is anaerobic and mostly nonviable during co-culture with DCs, it was tested whether some of the cellular components of Bb are effector molecules with iTreg-inducing activity.

As a result, among fractions of cell wall, cell membrane, and cytosol, only the cell surface extract effectively induced Treg cells. Treatment of the cell surface extract with RNase, DNase, Pronase, or boiling at high temperature did not reduce the Treg-inducing activity, which suggests that polysaccharides may be effector molecules. Actually, total cell surface polysaccharides (tCSPS) induced Treg cells in a dose-dependent manner (see FIGS. 11A and 11B).

tCSPS was separated by ion exclusion chromatography, followed by in-depth NMR analysis of fractions eluted at low ionic strength.

As a result, cell surface polysaccharides of *B. bifidum* consisted of at least 5 species (see FIG. 11C); beta-1-6-glucan (18%), beta-1-4-galactan (5%), beta-1-6-galactan (5%), beta-galactofuranan (2%), phospho glycero-β-galactofuran (PGβG) (64%) in different amounts (mol/mol). The polysaccharide PGβG is the most abundant in the total polysaccharides (64%), has an average molecular weight of 8000 Da, and is negatively charged, and the remaining four polysaccharides (β-1-6-glucan, β-1-4-galactan, β-1-6-galactan, and β-galactofuranan) had similar molecular weights (average ~4000 Da), and are not separately isolated any more.

Next, it was tested which polysaccharide among a neutral mixture of polysaccharides or PGβG has the activity to induce Treg cells in vitro. As a result, only neutral polysaccharides, not negatively charged polysaccharide PGβG, induced Treg cells (see FIG. 11D).

Therefore, the mixture of neutral polysaccharides derived from *B. bifidum* was named as "cell surface beta-glucan/galactan (CSGG)".

8-2: Identification of Treg Induction by CSGG

Figure 9:
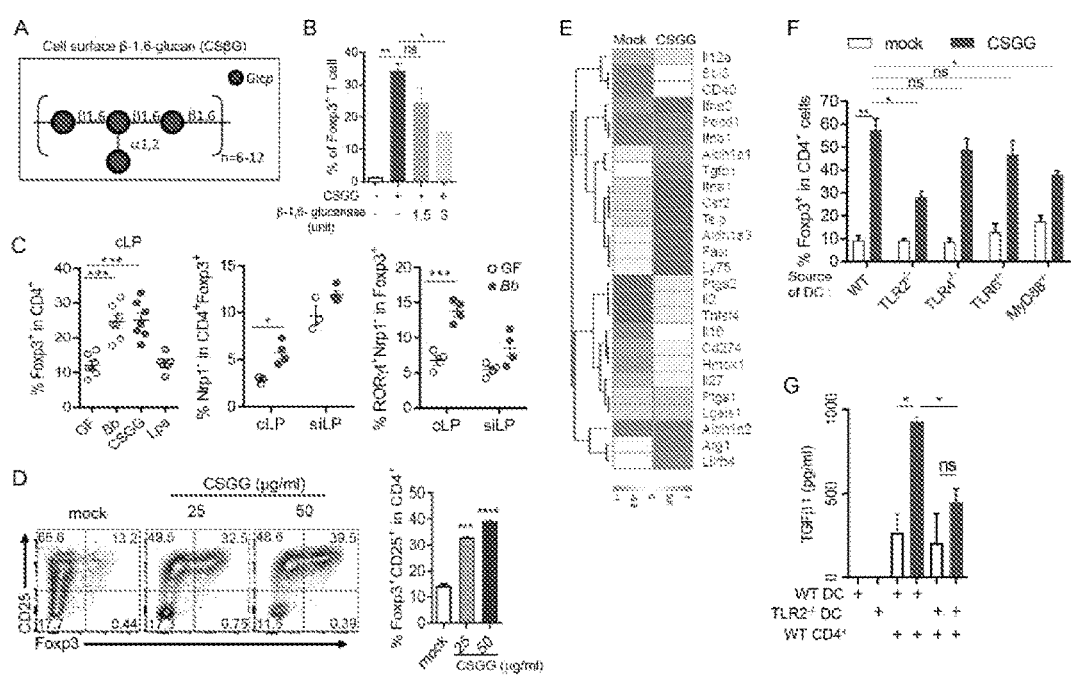
FIG. 9 illustrates the Treg cell induction mediation of cell surface beta-glucan/galactan polysaccharide (CSGG) of *B. bifidum*.
Figure 10:
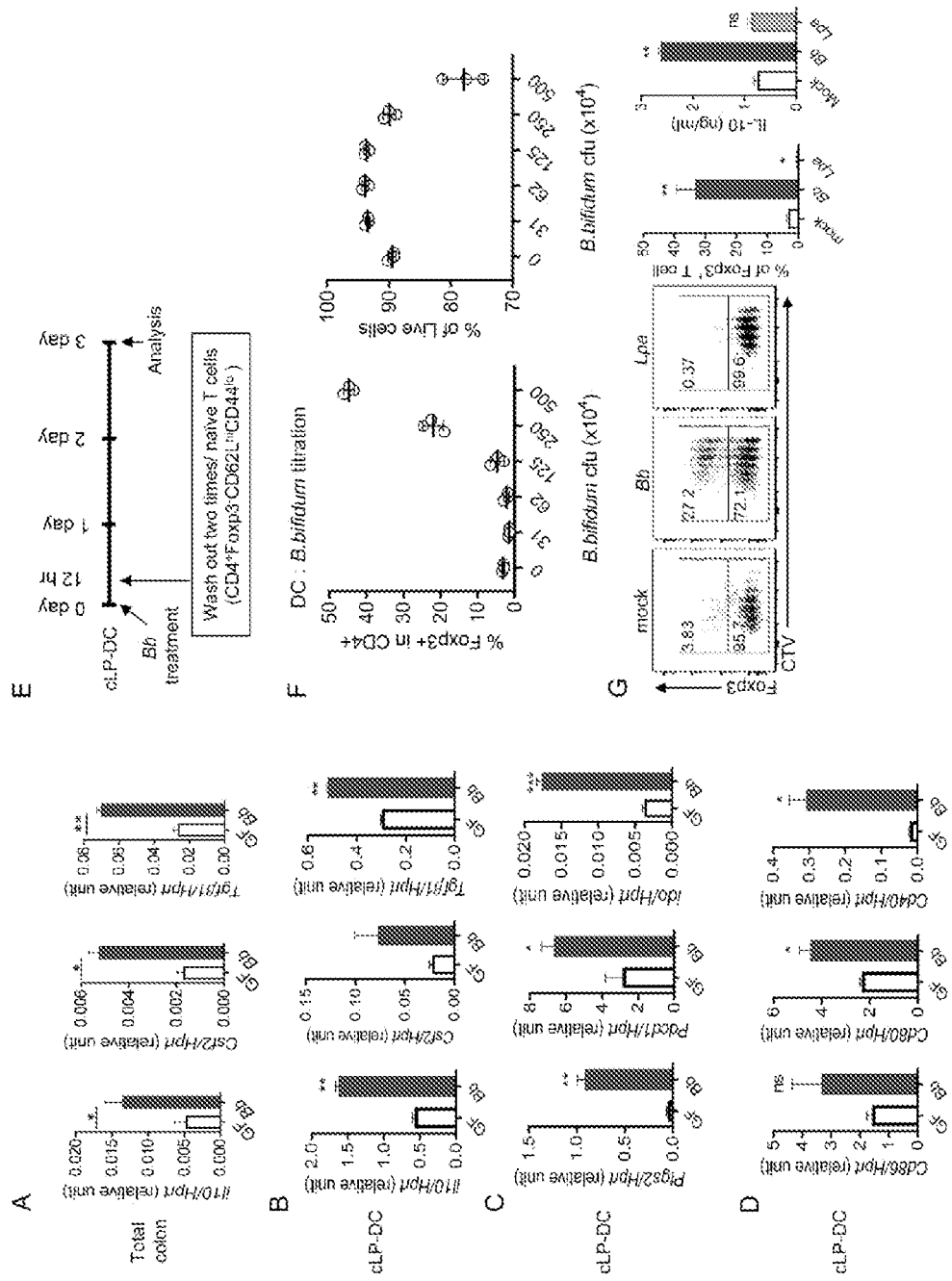
FIG. 10 illustrates the promotion of Treg cell induction through the DC-dependent mechanism of *B. bifidum*.
Figure 11:
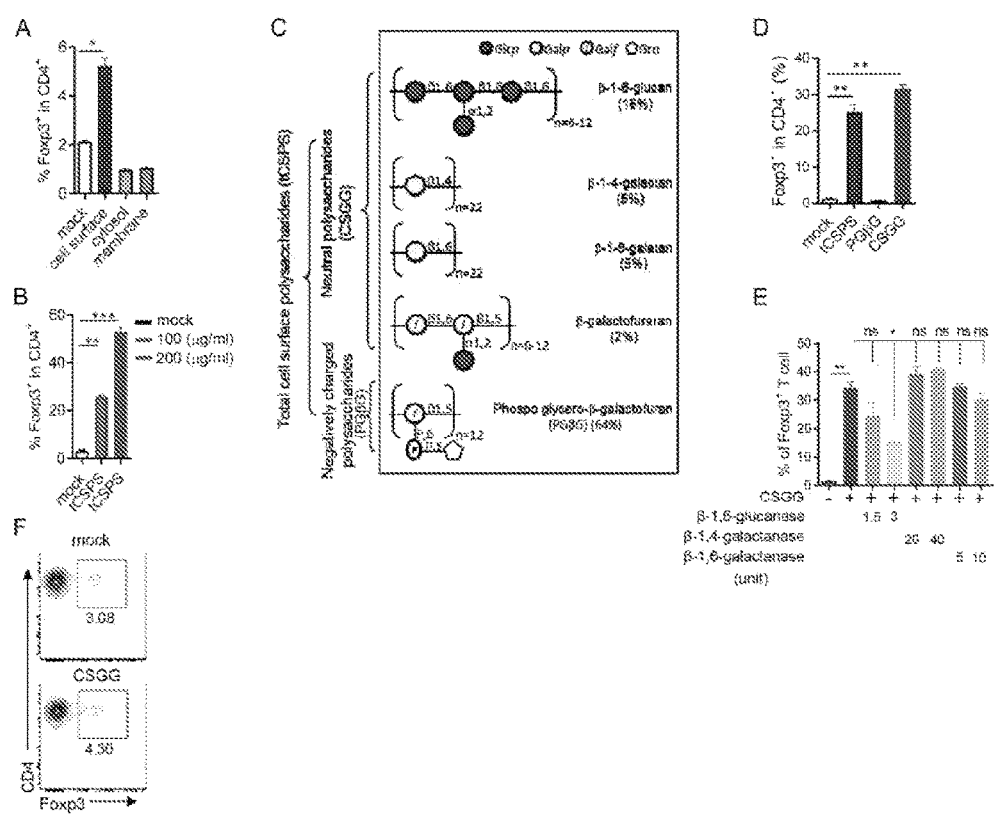
FIG. 11 illustrates the results of confirming beta-glucan/galactan polysaccharide (CSGG) as a core effector molecule of Treg cells induced by *B. bifidum*.

Among CSGG polysaccharides, cell surface β-1-6-glucan (CSβG) may be a key effector molecule because the level of CSGG-induced iTreg cells is reduced in a dose-dependent manner upon treatment with β-1,6-glucanase (see FIGS. 9A, 9B, and 11E). Moreover, co-culture of CSGG and naive CD4+ T cells in the absence of DCs failed to induce iTreg cells, from which it is shown that CSGG induces Treg cells through DC dependence (see FIG. 11F).

Figure 12:
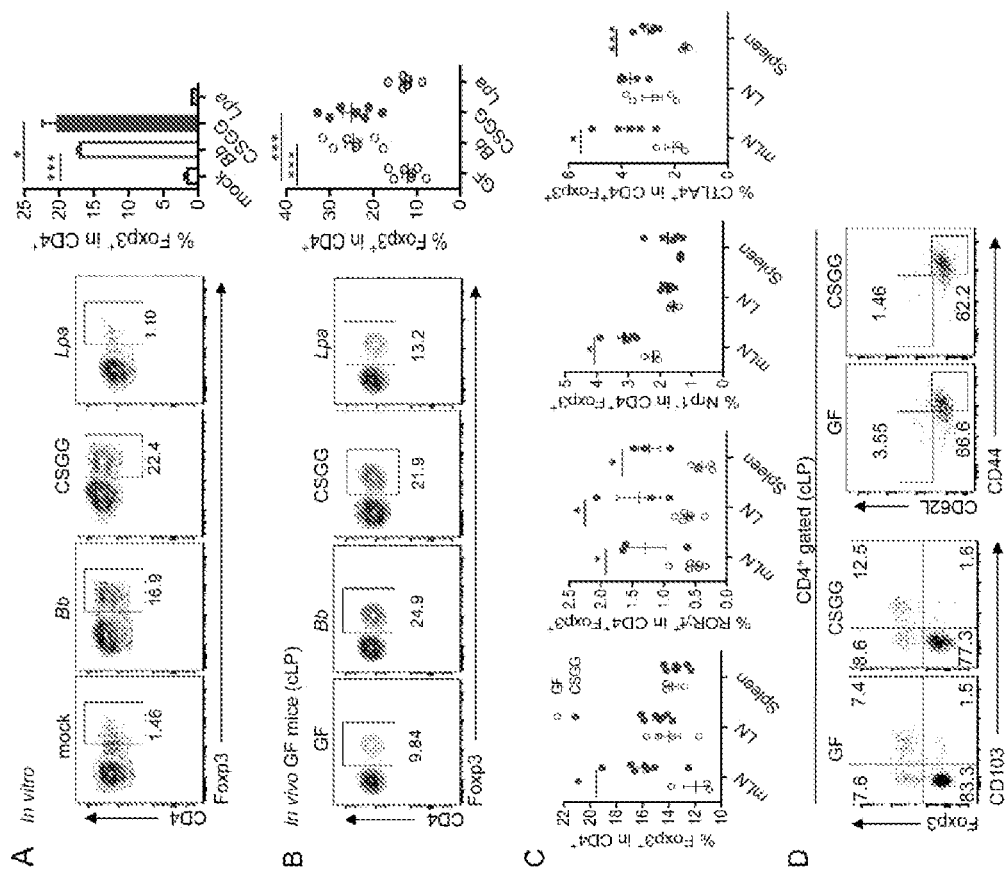
FIG. 12 illustrates Treg cell induction enhancement of CSGG in vitro and in vivo.

Next, it was tested whether CSGG can reproduce the capacity of whole bacteria to induce Treg cells in vitro and in vivo. CSGG-treated DCs induced Foxp3+ iTreg cells as effectively as *B. bifidum*-treated DCs in a dose-dependent manner (see FIG. 12A). As a result of intraperitoneal injection of CSGG (100 μg/dose) to GF mice 3 time for 3 weeks, CD4+Foxp3+ and Nrp1−Rorγt+ Treg cells were induced in cLP and mLN similar to *B. bifidum*-colonized mice (see FIGS. 9C, 12B, and 12C). These Treg cells exhibited a higher proportion of CD103+ and activated phenotype CD44$^{hi}$CD62$^{lo}$Foxp3+ than Treg cells from control GF mice (see FIG. 12D). Moreover, co-culturing of human DCs derived from PBMCs of healthy donors and naive CD4 T cells with CSGG induced CD25+Foxp3+ Treg cells in a dose-dependent manner (see FIG. 9D).

8-3: CSGG-Synthetic Gene Homology and Treg-inducing Activity

As known that the antiallergic effect of lactic acid bacteria depends on the strain and is affected by Th1/Th2 cytokine expression and balance (Fujiwara D et al., *Int Arch Allergy Immun*. 135(3):205-215, 2004), since the functional activity of probiotic bacteria is non-specific to species and strain-specific, it was tested whether all *B. bifidum* strains are able to induce iTreg cells, or only strains with high base homology to the *B. bifidum* PRI1 strain according to the present invention has iTreg-inducing activity. Whole genome sequencing of the *B. bifidum* PRI1 strain (GenBank accession number; CP018757) according to the present invention was performed and the base homology and Treg-inducing activity of expected orthologous genes related to CSGG synthesis and other *B. bifidum* genomes were compared.

As a result, the *B. bifidum* PRI1 of the present invention exhibited high homology to other *B. bifidum* strains. In particular, the strain A8 (Lopez P et al., *PLOS ONE*, 6(9): e24776, 2011) had similar activity to the *B. bifidum* PRI1 strain of the present invention, but exhibited deficiency in some orthologous genes related to CSGG synthesis and much lower Treg-inducing activity.

Example 9: Mechanism of rDC Production by CSGG

As observed in cLP-DC of mice colonized with *B. bifidum*, it was tested whether CSGG treatment induces modification of general DC phenotypes into regulatory DCs (rDCs). That is, to identify a fundamental mechanism of rDC production by CSGG, RNA-seq analysis was performed on CD11c$^+$ DCs treated with CSGG for 4 hours.

Figure 13:
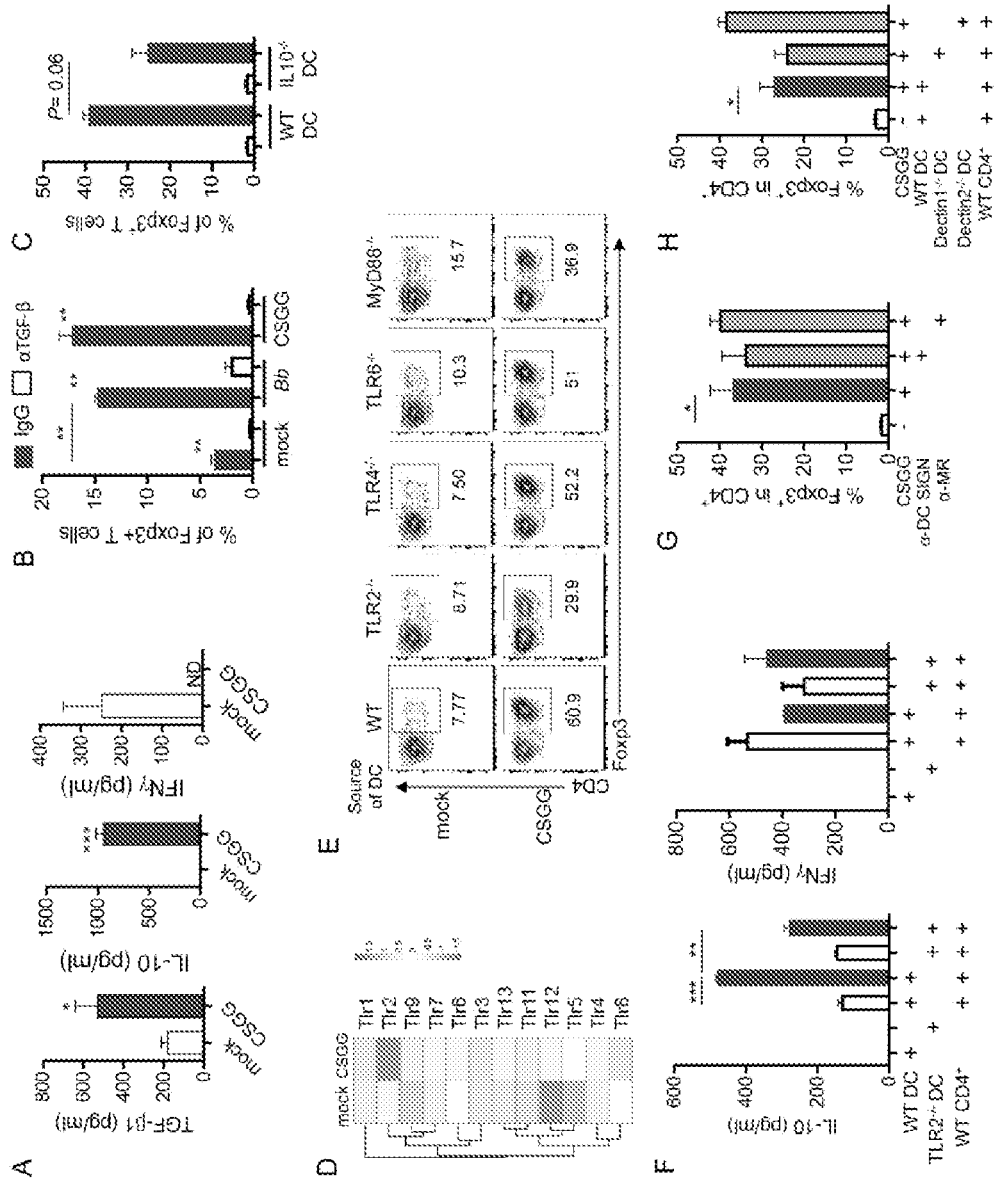
FIG. 13 illustrates the promotion of iTreg induction by CSGG through the production of TLR2-dependent regulatory DCs.

As a result, compared with mock control treatment, CSGG treatment significantly enhanced mRNA and protein levels of rDC-associated markers such as Ifna2, Pdcd1, Tgfβ1, Csf2, Ptgs2, Il10, and I127 (see FIGS. 9E and 13A).

CSGG treatment also significantly increases the protein levels of IL-10 and TGF-β, while reducing the level of IFN-γ. Compared with IL-10, TGF-β may play a pivotal role because the addition of anti-TGFβ-neutralizing antibody enables iTeg production induced by *B. bifidum* or CSGG treatment to be almost completely blocked (see FIGS. 13B and 13C). CSGG treatment selectively increased TLR2 expression (see FIG. 13D), and since TLR2$^{-/-}$ or Myd88$^{-/-}$ DCs exhibited a significant reduction in CSGG-mediated iTreg induction (see FIGS. 9F, 9G, and 13E), TLR2 and Myd88 may be major molecules that participate in CSGG recognition and signaling, among various pattern recognition receptors of DCs. TLR2-deficient DCs induced reduction of TGFβ1 and IL-10 in cultures (see FIG. 9G), but exhibited no change in IFNγ levels (see FIG. 13F). C-type lectin receptors (CLRs) may not be involved in CSGG-mediated iTreg cell production (see FIGS. 13G and 13H).

Example 10: Function of CSGG-Induced Treq Cells

The function of CSGG-induced Treg cells was examined in vitro and in vivo.

Since iTreg cells are often not functional or unstable in an inflammatory state, the immunosuppressive activity of iTreg cells induced by CSGG treatment and produced in vitro was tested. CD45.1$^+$CD4$^+$Foxp3$^-$ naive T cells were cultured with mock- or CSGG-treated DCs for 2 days, and then sorted to purify CD45.1$^+$CD4$^+$Foxp3$^+$ iTregs. CTV-labeled responder CD45.2$^+$CD4$^+$Foxp3$^-$ T cells were co-cultured with CD45.1$^+$ Treg cells at different rates, and then proliferation thereof was analyzed by FACS.

Figure 15:
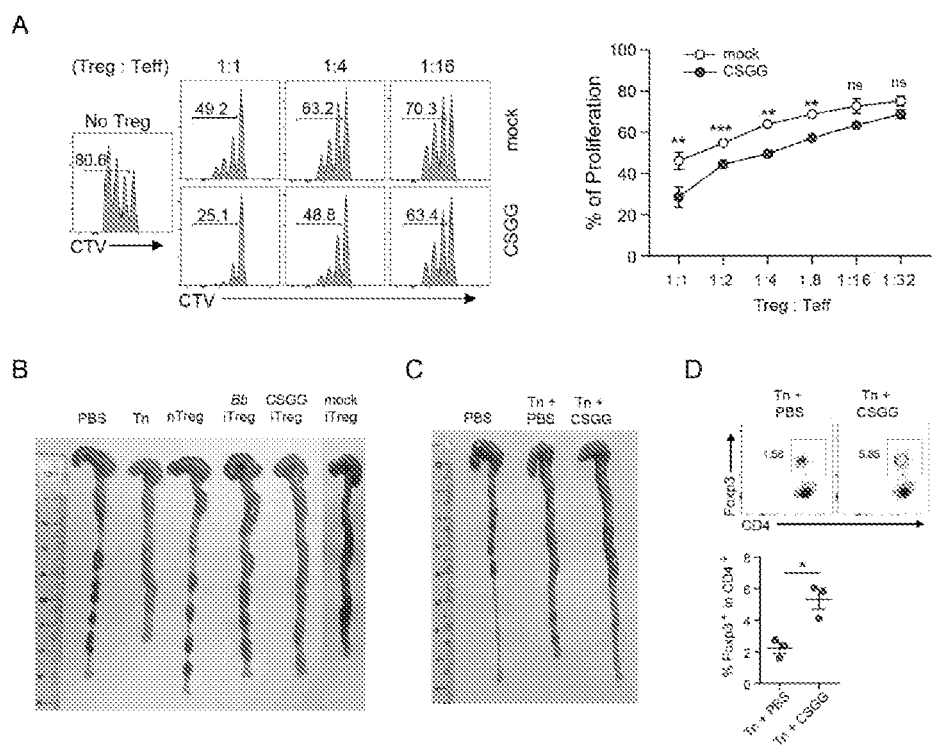
FIG. 15 illustrates the intestinal inflammation inhibitory function of CSGG-induced iTreg cells.

As a result, under in vitro conditions, iTreg cells generated and sorted in the presence of CSGG-treated DCs exhibited significantly enhanced immunosuppressive capacity compared to cells cultured with mock-treated DCs (see FIG. 15A).

Figure 14:
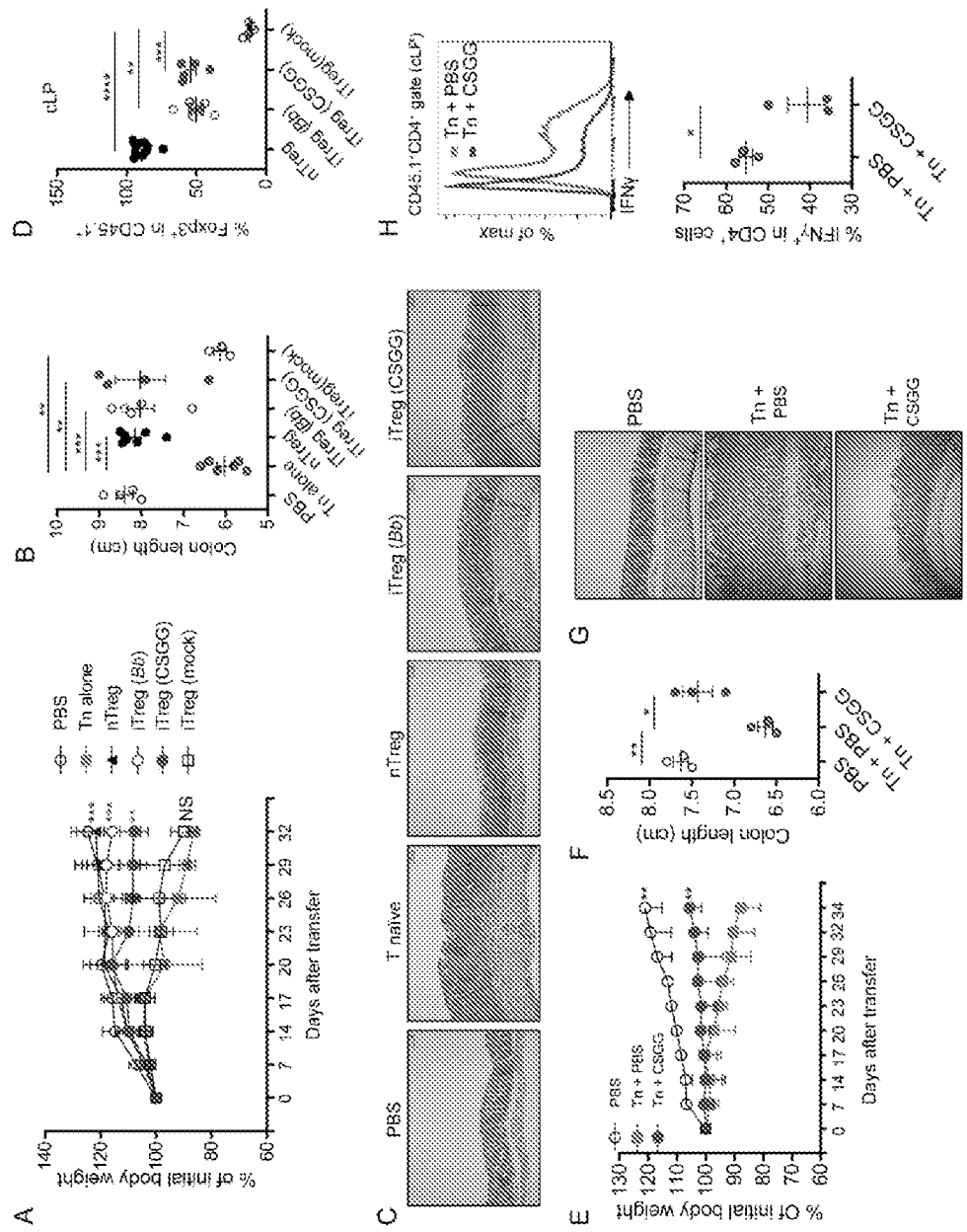
FIG. 14 illustrates the intestinal inflammation inhibitory function of CSGG-induced iTreg cells.

To test the inhibitory activity of Treg cells in vivo, a T cell transfer model of colitis was used. Naive CD4$^+$ T cells were transferred, to Rag1$^{-/-}$ lymphopenia mice, alone or in combination with allelically-marked (CD45.1) iTreg cells (see FIG. 14A).

As a result, co-injection of mock-induced iTreg cells was ineffective and failed to inhibit signs of colitis. Mice administered naive T cells alone also exhibited severe signs of colitis and weight loss within 3 weeks. In contrast, the transfer of *B. bifidum*- or CSGG-induced iTreg cells significantly reduced the development of colitis and significantly alleviated weight loss (see FIGS. 14A to 14D and 15B).

Example 11: Suppression of Colitis Development by CSGG Administration

To examine whether administration of CSGG itself can suppress colitis development, naive CD4$^+$Foxp3$^-$ T cells sorted from CD45.1$^+$Foxp3$^{GFP}$ mice were adoptively transferred into SPF Rag1$^{-/-}$ host mice, followed by intraperitoneal administration of PBS or CSGG (100 μg/dose) three times a week until the end of the experiment.

As a result, mice to which naive T cells were transferred, followed by PBS treatment developed severe colitis, whereas CSGG-administered mice significantly alleviated weight loss and significantly reduced histopathologically analyzed colitis progression (see FIGS. 14E to 14G and 15C). The protective effect of CSGG treatment is correlated with an increase in total Foxp3$^+$Treg cells and reduced frequency of IFN-γ-producing effector T cells (see FIGS. 14H and 15C). These results suggest that CD4$^+$Foxp3$^+$ Treg cells induced by CSGG treatment are able to suppress the progression of inflammatory colitis.

[Accession Number]

Depositary organization name: Korea Research Institute of Bioscience and Biotechnology Accession number: KCTC13270BP Accession date: 20170519

INDUSTRIAL APPLICABILITY

Polysaccharides according to the present invention, e.g., cell surface beta glucan/galactan polysaccharide (CSGG) and *Bifidobacterium bifidum* PRI1 (KCTC13270BP) producing the CSGG can induce Treg cells by various antigens, and thus the strain, the CSGG, or the induced Treg cell is useful for the prevention or treatment of an immune disease or an inflammatory disease.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method of treating an immune disease or an inflammatory disease, comprising administering a pharmaceutical composition containing a *Bifidobacterium bifidum* PRI1 (KCTC13270BP) or a polysaccharide obtained from the *Bifidobacterium bifidum* PRI1 as an active ingredient to a subject in need thereof;
   wherein the polysaccharide comprises a β-1-6-glucan,
   wherein the β-1-6-glucan comprises β-1,6-glycosidic linked glucose backbone and α-1,2-glycosidic linked glucose side chain.

2. A method of treating or alleviating an immune disease or an inflammatory disease, comprising administering a food containing a *Bifidobacterium bifidum* PRI1 (KCTC13270BP) or a polysaccharide obtained from the *Bifidobacterium bifidum* PRI1 to a subject in need thereof,
   wherein the polysaccharide comprises a β-1-6-glucan,
   wherein the β-1-6-glucan comprises β-1,6- glycosidic linked glucose backbone and α-1,2-glycosidic linked glucose side chain.

3. The method according to claim 1, wherein the β-1-6-glucan has a molecular weight of 3 kDa to 5 kDa.

4. The method according to claim 1, wherein the polysaccharide further comprises β-1-4-galactan, β-1-6-galactan, or β-galactofuranan.

5. The method according to claim 4, wherein a content ratio (molar ratio) of the β-1-6-glucan, β-1-4-galactan, β-1-6-galactan, and β-galactofuranan is 5-50:2-15:2-15:1-5.

6. The method according to claim 1, wherein the polysaccharide is a mixture having a molecular weight of 100 kDa or less.

7. The method according to claim 1, wherein a charge of the polysaccharide is neutral.

8. The method according to claim 1, wherein the *Bifidobacterium bifidum* PRI1 (KCTC13270BP) or the polysaccharide induces regulatory T (Treg) cells.

9. The method according to claim 8, wherein the regulatory T (Treg) cells are CD4$^+$Foxp3$^+$ Treg cells.

* * * * *